US010874612B2

(12) United States Patent
Dormer et al.

(10) Patent No.: US 10,874,612 B2
(45) Date of Patent: Dec. 29, 2020

(54) BIODEGRADABLE POLYMER MICROSPHERE COMPOSITIONS FOR PARENTERAL ADMINISTRATION

(71) Applicant: ADARE PHARMACEUTICALS USA, INC., Lawrenceville, NJ (US)

(72) Inventors: Nathan Dormer, Mission, KS (US); Cory Berkland, Lawrence, KS (US)

(73) Assignee: Adare Pharmaceuticals USA, Inc., Lawrenceville, NJ (US)

(*) Notice: Subject to any disclaimer, the term of this patent is extended or adjusted under 35 U.S.C. 154(b) by 104 days.

(21) Appl. No.: 16/172,134

(22) Filed: Oct. 26, 2018

(65) Prior Publication Data
US 2019/0060238 A1    Feb. 28, 2019

Related U.S. Application Data

(63) Continuation of application No. PCT/US2017/029510, filed on Apr. 26, 2017.
(Continued)

(51) Int. Cl.
*A61K 9/16* (2006.01)
*A61K 31/00* (2006.01)
(Continued)

(52) U.S. Cl.
CPC .......... *A61K 9/1652* (2013.01); *A61K 9/0019* (2013.01); *A61K 9/1647* (2013.01);
(Continued)

(58) Field of Classification Search
CPC .... A61K 9/1652; A61K 31/00; A61K 9/0019; A61K 9/1647; A61K 45/06; A61K 9/19;
(Continued)

(56) References Cited

U.S. PATENT DOCUMENTS 5,017,378 A   5/1991 Turner et al.
5,538,739 A   7/1996 Bodmer et al.
(Continued)

FOREIGN PATENT DOCUMENTS

CN     101396338 A     4/2009
WO     9522318 A1      8/1995
WO     2005007122 A2   1/2005

OTHER PUBLICATIONS

Cilurzo et al., "Design on methylprednisolone biodegradable microspheres intended for intra-atricular administration" AAPS PharmSci Tech, vol. 9, No. 4, pp. 1136-1142, Dec. 1, 2008; abstract; pp. 1137-1138; 1140-1141.
(Continued)

*Primary Examiner* — Trevor Love
(74) *Attorney, Agent, or Firm* — Cooley, LLP

(57) ABSTRACT

Novel microsphere compositions for use in parenteral formulations are provided. The microspheres comprise a biodegradable polymer of a molecular weight greater than 10,000 daltons, an active therapeutic agent, and a cellulose-derived material such as ethyl cellulose, carboxymethyl cellulose, hydroxypropylmethyl cellulose, or sodium carboxymethyl cellulose. The microsphere compositions decreased deviation in mean microsphere diameter, improved drug entrapment, and improved microsphere stability.

16 Claims, 21 Drawing Sheets
(21 of 21 Drawing Sheet(s) Filed in Color)

Related U.S. Application Data

(60) Provisional application No. 62/327,775, filed on Apr. 26, 2016.

(51) Int. Cl.
| | | |
|---|---|---|
| *A61K 9/00* | (2006.01) | |
| *A61K 9/19* | (2006.01) | |
| *A61K 45/06* | (2006.01) | |
| *A61P 5/24* | (2006.01) | |
| *A61P 43/00* | (2006.01) | |
| *A61P 35/00* | (2006.01) | |
| *A61P 33/02* | (2006.01) | |
| *A61P 31/18* | (2006.01) | |
| *A61P 3/02* | (2006.01) | |
| *A61K 31/567* | (2006.01) | |
| *A61K 31/47* | (2006.01) | |

(52) U.S. Cl.
CPC .............. *A61K 31/00* (2013.01); *A61K 45/06* (2013.01); *A61K 9/19* (2013.01)

(58) Field of Classification Search
CPC ...... A61K 31/567; A61K 31/47; A61K 38/31; A61P 5/24; A61P 43/00; A61P 35/00; A61P 33/02; A61P 31/18; A61P 3/02
See application file for complete search history.

(56) References Cited

U.S. PATENT DOCUMENTS

| | | |
|---|---|---|
| 5,679,377 A | 10/1997 | Bernstein et al. |
| 8,481,059 B2 | 7/2013 | Cleary et al. |
| 9,289,390 B2 | 3/2016 | Folger et al. |
| 2008/0233201 A1 | 9/2008 | Royere et al. |
| 2014/0294986 A1 | 10/2014 | Liu et al. |
| 2014/0328793 A1 | 11/2014 | Gavegnano et al. |
| 2015/0209342 A1 | 7/2015 | Lu et al. |
| 2015/0359804 A1 | 12/2015 | Dormer et al. |

OTHER PUBLICATIONS

Panusa et al., "Methylprednisolone-loaded PLGA microspheres: A new formulation for sustained release via intra-aticular administration. A comparison study with methylprednisolone acetate in rats" Jouranl of Pharmaceutical Sciences, vol. 100, No. 11, pp. 4580-4586, Nov. 11, 2011; abstract; pp. 4581, 4583.
The Supplementary European Search Report dated Nov. 20, 2019 in Application No. 17790301.0.

BIODEGRADABLE POLYMER MICROSPHERE COMPOSITIONS FOR PARENTERAL ADMINISTRATION

This application is a continuation of International Application No. PCT/US17/29510, filed Apr. 26, 2017, and claims priority to U.S. Provisional Patent Application Ser. No. 62/327,775 filed on Apr. 26, 2016, the contents of which are incorporated herein by reference thereto.

BACKGROUND

Cellulose ethers and esters such as ethyl cellulose are water insoluble binders used widely in oral drug formulation (such as tablets, pills, capsules) for their ability to intercalate material matrices and provide physical integrity and humidity resistance. Ethyl cellulose is a material that is generally recognized as safe (GRAS) for oral drug formulation. Ethyl cellulose is not, however, used in parenteral drug formulation.

Biodegradable polymers such as polylactides, polylactide-co-glycolides and polyanhydrides have been used in parenteral drug formulations. They have also been used in some wound healing powders applied topically.

SUMMARY

The present disclosure outlines the benefits of including cellulose derivatives such as ethyl cellulose in combination with biodegradable polymers that are used exclusively in parenteral drug formulation.

The present disclosure relates to novel microsphere compositions for parenteral administrations. The compositions comprise a plurality of microspheres, wherein each microsphere comprises a homogenous mixture of a biodegradable polymer, an active therapeutic agent, and a cellulose-derived material, and wherein the biodegradable polymer has a molecular weight of greater than 10,000 Daltons.

Embodiments include:

The composition wherein the percentage of biodegradable polymer is from about 50% to about 95% w/w of each microsphere.

The composition wherein the biodegradable polymer comprises a bulk-eroding polymer; such as wherein the biodegradable polymer comprises a polyester polymer comprising lactide, glycolide, or a combination thereof as a co-block polymer; wherein the biodegradable polymer comprises a polyester polymer comprising a co-block polymer selected from the group consisting of poly(D,L-lactide-co-glycolide) and poly(L-lactide-co-glycolide); the composition wherein the co-block polymer is poly(D,L-lactide-co-glycolide); preferably wherein the percentage of lactide is from about 65% to about 85% w/w of the co-block polymer and wherein the percentage of glycolide is from about 15% to about 35% w/w of the co-block polymer; the composition wherein the co-block polymer is poly(L-lactide-co-glycolide); preferably wherein the percentage of lactide is from about 65% to about 85% w/w of the co-block polymer and wherein the percentage of glycolide is from about 15% to about 35% w/w of the co-block polymer; and/or the composition wherein the polyester polymer comprises poly(D,L-lactide-co-glycolide) and poly(D,L-lactide).

The composition wherein the biodegradable polymer comprises a surface-eroding polymer; such as wherein the biodegradable polymer comprises a polyanhydride polymer; including wherein the polyanhydride polymer comprises 1,ω-bis(carboxy)($C_2$-$C_{10}$)alkane units, 1,ω-bis(carboxyphenoxy)($C_2$-$C_{10}$)alkane units, or combinations thereof; and/or the composition wherein the polyanhydride polymer comprises a copolymer of sebacic anhydride and 1,3-bis(p-carboxyphenoxy)propane, 1,6-bis-(p-carboxy-phenoxy) hexane, or 1,8-bis(carboxyphenoxy)-3,6-dioxaoctane, or combinations thereof.

The composition of any of the preceding embodiments wherein the percentage of cellulose-derived material is from about 0.5% to about 6% w/w of each microsphere; the composition wherein the cellulose-derived material comprises ethyl cellulose, carboxymethyl cellulose, hydroxypropylmethyl cellulose, sodium carboxymethyl cellulose or combinations thereof; notably wherein the cellulose-derived material comprises ethyl cellulose.

The composition of any of the preceding embodiments wherein the cellulose-derived material (CDM) comprises a viscosity fraction of about 0.1% to about 5%; wherein the viscosity fraction is calculated according to the equation $$vf\_CDM = \eta\_inh\_CDM*(f\_CDM)/[\eta\_inh\_CDM*(f\_CDM) + \eta\_inh\_Pol*(f\_Pol)]*100$$

wherein vf_CDM=the viscosity fraction of CDM in the polymer matrix; η_inh_CDM=the inherent viscosity of the CDM; η_inh_Pol=the inherent viscosity of the polymer, f_CDM=the fraction of CDM in the polymer matrix; and f_Pol=the fraction of polymer in the polymer matrix; such as wherein the CDM comprises ethyl cellulose and comprises a viscosity fraction of about 0.1% to about 5%; about 0.5% to about 3.5%; about 0.2% to about 2%; about 0.3% to about 1%; or about 0.5% to about 2%.

The composition of any of the preceding embodiments wherein the percentage of active therapeutic agent is from about 10% to about 40% w/w of each microsphere; including the composition wherein the active therapeutic agent is an integrase inhibitor; the composition wherein the active therapeutic agent is an antiparasitic; the composition wherein the active therapeutic agent is a steroid hormone; the composition wherein the active therapeutic agent is a somatostatin analogue; the composition wherein the active therapeutic agent is a peptide; and/or the composition wherein the active therapeutic agent is an organic compound having a molecular weight of less than 1000 daltons.

The composition of any of the preceding embodiments wherein the plurality of microspheres are suspended in an aqueous carrier.

The composition of any of the preceding embodiments wherein the plurality of microspheres are suspended in a non-aqueous carrier.

The composition of any of the preceding embodiments further comprising a gel, wherein the plurality of microspheres are dispersed in the gel.

The composition of any of the preceding embodiments wherein at least 90% of the plurality of microspheres have particle diameters from about 40 μm to about 70 μm; wherein at least 90% of the plurality of microspheres have particle diameters from about 45 μm to about 65 μm; wherein at least 90% of the plurality of microspheres have particle diameters from about 50 μm to about 60 μm; wherein at least 90% of the plurality of microspheres have particle diameters from about 50 μm to about 70 μm; wherein at least 90% of the plurality of microspheres have particle diameters from about 40 μm to about 55 μm; wherein at least 90% of the plurality of microspheres have particle diameters from about 60 μm to about 100 μm; wherein at least 90% of the plurality of microspheres have particle diameters from about 65 μm to about 95 μm; wherein at least 90% of the plurality of microspheres have particle diameters from about 70 µm to about 90 µm; wherein at least 90% of the plurality of microspheres have particle diameters from about 70 µm to about 85 µm; wherein at least 90% of the plurality of microspheres have particle diameters from about 70 µm to about 80 µm; wherein at least 90% of the plurality of microspheres have particle diameters from about 75 µm to about 85 µm.

The composition of any of the preceding embodiments sufficient to release the active therapeutic agent over a period of at least 100 days; sufficient to release the active therapeutic agent over a period of from about 80 days to about 120 days; sufficient to release at least 50% of the active therapeutic agent over a period of at least 50 days; sufficient to release at least 60% of the active therapeutic agent over a period of at least 100 days; and/or sufficient to release at least 10% of the active therapeutic agent over a period of at least 50 days.

This invention also provides a pharmaceutical composition including a microsphere of any of the previous embodiments, and optionally a pharmaceutically acceptable carrier and/or excipient.

Embodiments include those wherein the composition is formulated for parenteral administration and further comprises at least one member selected from the group consisting of an aqueous solution and a buffer solution; wherein the composition further comprises a pharmaceutical surfactant and/or wherein the composition further comprises a cryoprotectant.

This invention also provides a method for treating a subject having a disease or condition, the method comprising administering a composition of any of the preceding embodiments to the subject parenterally.

Embodiments include those wherein the subject has a disease or condition indicating a need for treatment comprising parenteral administration of an integrase inhibitor, an antiparasitic, a steroid hormone, a somatostatin analogue, a peptide or an organic compound having a molecular weight of less than 1000 daltons.

BRIEF DESCRIPTION OF THE FIGURES

The patent or application file contains at least one drawing executed in color. Copies of this patent or patent application publication with color drawing(s) will be provided by the Office upon request and payment of the necessary fee. Some specific example embodiments of the disclosure may be understood by referring, in part, to the following description and the accompanying drawings.

DETAILED DESCRIPTION

Figure 1A:
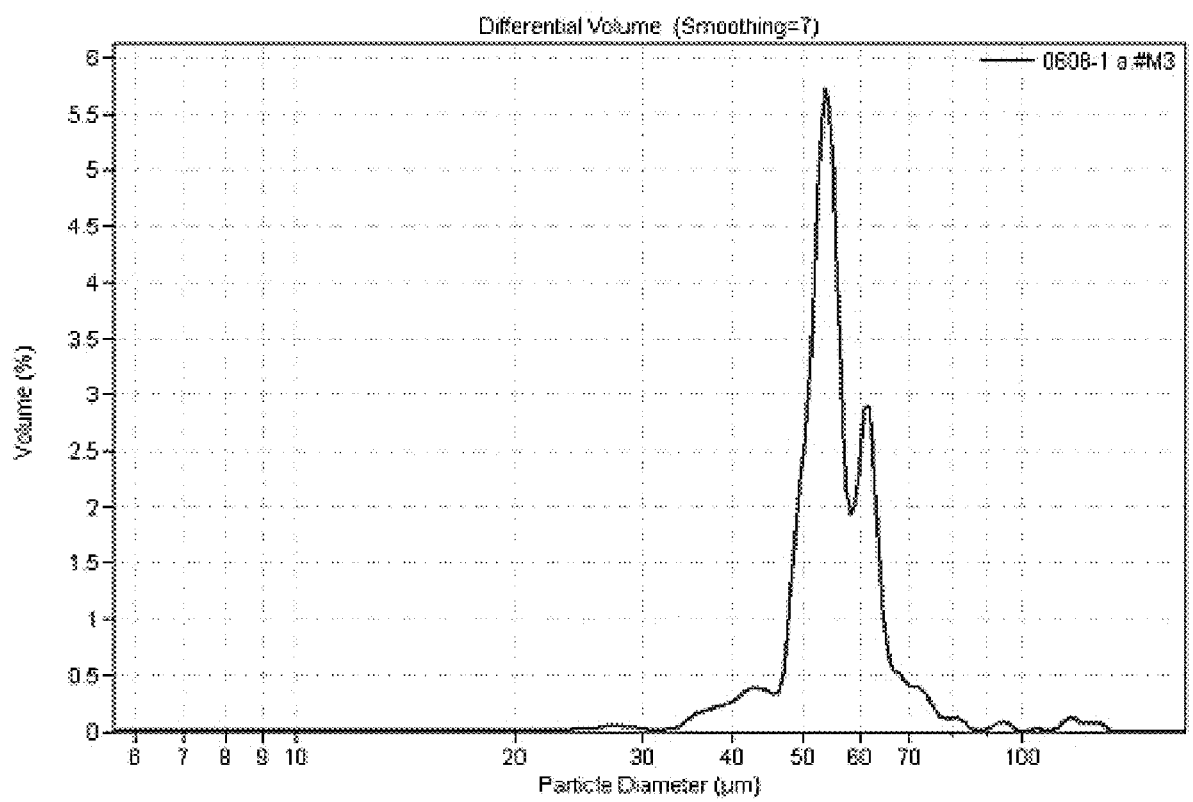
FIGS. 1A to 1E show plots of particle size distribution and photomicrographs of microspheres prepared in Example 1.
Figure 1A:
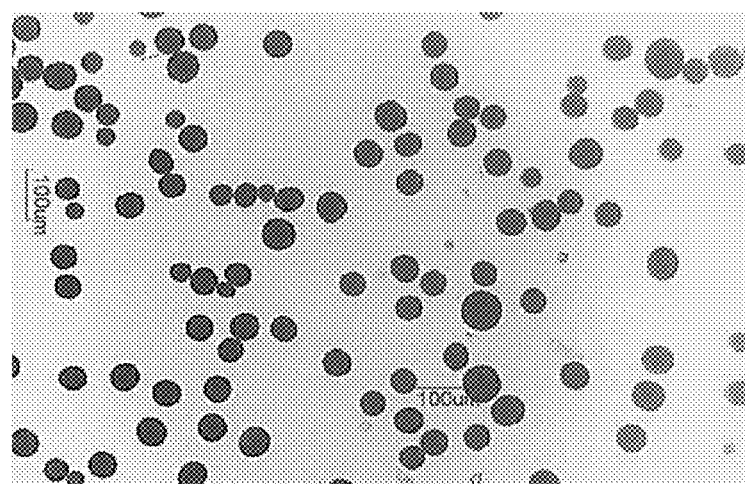

The term "and/or" means any one of the items, any combination of the items, or all of the items with which this term is associated. The singular forms "a," "an," and "the" include plural reference unless the context clearly dictates otherwise. Accordingly, the indefinite articles "a" or "an", as used in the claims, are defined herein to mean one or more than one of the element that it introduces. Thus, for example, a reference to "a compound" includes a plurality of such compounds, so that a compound X includes a plurality of compounds X. It is further noted that the claims may be drafted to exclude any optional element, i.e. an optional element may or may not be present in the claimed embodiment. As such, this statement is intended to serve as antecedent basis for use of such exclusive terminology as "solely," "only," and the like in connection with the recitation of claim elements, or use of a "negative" limitation.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. When ranges are expressed as ranging from one or more lower limit(s) to one or more upper limit(s), ranges comtemplated may range from any of the enumerated lower limits to any of the enumerated upper limits.

While compositions and methods are described in terms of "comprising," "containing," or "including" various components or steps, the compositions and methods can also "consist essentially of" or "consist of" the various components and steps. All numbers and ranges disclosed above may vary by some amount. Also, the terms in the claims have their plain, ordinary meaning unless otherwise explicitly and clearly defined herein. If there is any conflict in the usages of a word or term in this specification and one or more patent or other documents that may be incorporated herein by reference, the definitions that are consistent with this specification should be adopted.

As used herein, the term "biodegradable" refers to the ability of a composition to be broken down, particularly into innocuous products by the action of living organisms. In particular, it means that the polymer can break down or degrade within the body to non-toxic components after all bioactive agent or diagnostic agent has been released. "Biocompatible" means materials, or the intermediates, or end products of materials that are formed by solubilization hydrolysis, or by the action of biologically formed entities such as enzymes or other products of the organism, and which cause no adverse effect on the body.

As used herein, the term "hydrophilic" refers to a chemical group having a tendency to repel non-polar or uncharged chemical groups, e.g., hexane, and to attract polar or charged chemical groups, e.g., water. "Hydrophilic" also refers to a chemical that tends to dissolve in, mix with, or be wetted by water. "Hydrophilic" embraces an agent that is preferably sparingly soluble, soluble, freely soluble, or very soluble, according to USP-NF definitions. As used herein, the term "hydrophobic" refers to a chemical group having a tendency to attract non-polar or uncharged chemical groups, e.g., hexane, and to repel polar or charged chemical groups, e.g., water. "Hydrophobic" also refers to a chemical that tends not to dissolve in, mix with, or be wetted by water. As used herein, the term "amphiphilic" is used to describe a chemical compound as possessing both hydrophilic and lipophilic hydrophobic properties.

The terms "drug" or "active agent" or "therapeutic agent" or "bioactive agent" or "diagnostic agent" shall mean any inorganic or organic compound or substance having physiologically or pharmacologically activity that acts locally and/or systemically in the body (bioactivity) and is adapted or used for a therapeutic or diagnostic purpose. Any of these terms are used herein to refer to a substance that is administered to a patient for the treatment (e.g., therapeutic agent), prevention (e.g., prophylactic agent), or diagnosis (e.g., diagnostic agent) of a disease or disorder.

As used herein the phrase "therapeutically effective amount" (or more simply "effective amount") includes an amount of bioactive agent or diagnostic agent sufficient to provide a specific therapeutic or diagnostic response for which the drug is administered to a patient in need of particular treatment, at a reasonable risk/benefit ratio as would attend any medical treatment or diagnostic test. The therapeutic effect could be any therapeutic effect ranging from prevention, symptom amelioration, symptom treatment, to disease termination or cure. The skilled clinician will recognize that the therapeutically effective amount of drug will depend upon the patient, the indication or disease, the treatment being effected, and the particular drug administered.

The terms "treatment" or "treating" means administration of a drug for purposes including: (i) inhibiting the disease or condition, that is, arresting the development of clinical symptoms; (ii) relieving the disease or condition, that is, causing the regression of clinical symptoms and/or (iii) preventing the disease or condition, that is, causing the clinical symptoms of the disease or condition not to develop. As used herein, the terms also mean administration of a diagnostic agent useful for detection of a condition in a subject that is indicative or characteristic of a disease or disorder. As used herein, the term "prevention" refers to a forestalling, including temporary forestalling, of the onset of a disorder. As used herein, the term "indicative" means to have the characteristics of a certain disease or to suggest the presence of status of a certain disease. As used herein, "administering" and similar terms mean delivering the composition to an individual being treated.

"Parenteral" shall mean any route of administration other than the alimentary canal and shall specifically include intramuscular, intraperitoneal, intra-abdominal, subcutaneous, and, to the extent feasible, intravenous.

"Pharmaceutically acceptable" means that which is useful in preparing a pharmaceutical composition and is generally safe, non-toxic, and neither biologically nor otherwise undesirable and includes that which is acceptable for veterinary use as well as human pharmaceutical use. Examples of "pharmaceutically acceptable liquid carriers" include water, organic solvents, gels, creams and the like. Preferred pharmaceutically acceptable aqueous liquids or solutions include phosphate buffered saline (PBS), saline, and dextrose solutions.

"Peptide", "polypeptide", "oligopeptide," and "protein" are used interchangeably herein when referring to peptide or protein agents and shall not be limited as to any particular molecular weight, peptide sequence or length, field of bioactivity, diagnostic use, or therapeutic use unless specifically stated. However, preferred proteins and peptides have molecular weights ranging from about 1 kDa to 500 kDa (e.g., about 1, 10, 50, 100, 150, 200, 250, 300, 350, 400, 450, or 500 kDa or some range therebetween).

"Small molecule," as used herein, refers to molecules with a molecular weight of less than about 2000 daltons (g/mol), such as less than about 1500 daltons, less than about 1000 daltons, or less than about 600 daltons.

The term "polymer" refers to a molecule of one or more repeating monomeric residue units covalently bonded together by one or more repeating chemical functional groups. The term includes all polymeric forms such as linear, branched, star, random, block, graft and the like. It includes homopolymers formed from a single monomer, copolymers formed from two or more monomers, terpolymers formed from three or more polymers and other polymers formed from more than three monomers. Differing forms of a polymer may also have more than one repeating, covalently bonded functional group.

The microspheres described herein, wherein the polymers described herein are combined with a cellulose-derived material and a therapeutic agent, can be used to provide drug delivery systems or devices, or pharmaceutical compositions.

The composition of the invention comprises microspheres comprising (a) a biodegradable polymer such as poly(DL-lactide) poly(DL-lactide-co-glycolide) and/or polyanhydrides, (b) cellulose-derived material; and (c) at least one pharmacologically active substance.

In the simplest systems, microspheres are comprised of a polymer constituent and a drug constituent by dissolving the polymer in an organic solvent and either co-solubilizing the drug or suspending the drug in the same phase. Microspheres may be manufactured by forming droplets of the drug/polymer/organic (discontinuous) phase in a non-solvent (continuous) phase. Droplet formation can be random (such as in emulsion technologies) or highly controlled (such as in precision particle fabrication technology). When the microsphere constituents consist only of polymer and solvent, droplet formation and shape uniformity is a function of the solvent, polymer, and continuous phase. When the microsphere constituents also contain a drug, droplet formation and shape uniformity will also depend on the drug and its solubility in the continuous and discontinuous phases. As drug fraction increases, the ability of the droplets to solidify and form uniform spherical shapes can become more difficult if the physicochemical properties of the drug and polymer are very dissimilar, as the case with most drug-polymer systems. When a cellulose-derived material such as a cellulose ether or cellulose ester (e.g. ethyl cellulose) is included with the biodegradable polymers at specific ranges of viscosity fractions, the present disclosure reveals many advantages, such as decreased deviation in mean microsphere diameter, improved drug entrapment, and improved microsphere stability as inferred from dissolution behavior.

Biodegradable Polymers

The biodegradable polymer may be a bulk-eroding polymer such as a polyester polymer.

The polyester polymer may comprise lactide, glycolide, or a combination thereof as a co-block polymer, such as wherein the percentage of lactide is from about 65% to about 85% w/w of the co-block polymer and wherein the percentage of glycolide is from about 15% to about 35% w/w of the co-block polymer. More specifically, the polyester polymer is selected from the group consisting of poly(D,L-lactide), poly(D,L-lactide-co-glycolide), poly(L-lactide-co-glycolide), poly(D,L-lactide-co-glycolide), and combinations thereof.

Biodegradable polymers that are applicable include those comprised of lactide and glycolide species, including but not limited to: polylactides, polyglycolides, poly(D,L-lactide-co-glycolide), poly(L-lactide-co-glycolide), poly(D,L-lactide), and poly(ε-caprolactone).

Polylactides (PLA), also called polylactic acids, are polyesters on the basis of lactic acid. Polylactides are polyhydroxyacids. They are biocompatible and biodegradable. The lactide may comprise a racemic mixture of D and L-isomers, providing a D,L-lactide. The lactide may also be obtained wherein the D:L ratio is different from 1:1 (enriched mixtures). Moreover, it is possible to prepare either of the single D- or L-enantiomers in substantially pure form (>99.99% by weight). Among the two enantiomeric forms of the lactide, the L-isomer is preferred. In the case of enriched mixtures of lactides used in preparing lactide-containing biopolymers, those enriched in the L-enantiomer are preferred, preferably with an L:D ratio of the two enantiomers ranging from 51:49 to 99.99:0.01 by weight, such as 60:40, 75:25, 80:20, or 90:10. As used herein, when a polymer is designated as comprising L-lactide, at least 60, or at least 75, or at least 80, or at least 90% of the lactide therein comprises the L-enantiomer.

Polylactides may also include block copolymers comprising blocks of L-lactide and D,L lactide.

The properties of polylactides depend primarily on their molecular weight, degree of chirality, degree of crystallinity, and the portion of copolymers, if applicable. The glass transition temperature, the melting temperature, the tensile strength and the E-module of the polylactides increase, but the breaking elongation decreases as the molecular weight of the polylactides increases.

Polylactides can be obtained by ring-opening polymerization of lactide. The ring-opening polymerisation is performed at temperatures between 140 and 180° C. in the presence of stannous octoate catalyst. Polylactides with high molecular weight can be easily produced by this method. In addition, high molecular weight and pure polylactides can be generated directly from lactic acid by the so-called polycondensation.

Polylactide-co-glycolides (PLGA) are biodegradable polymers that comprise (or consist of) lactic acid linked with glycolic acid, the respective percentages of which play a major role in the rate of drug release. The ratio of lactide to glycolide may be from 90:10 to 10:90, with ratios of from 20:80 to 80:20 being preferred and ratios of from 40:60 to 60:40 being more preferred, and a ratio of 50:50 being most preferred. Lactide is optically active, and any proportions of D and L isomers may be present in the copolymer, ranging from pure D-lactide to pure L-lactide, with racemates comprising 50% D-lactide and 50% L-lactide.

The biodegradable polymer may comprise a surface-eroding polymer; such as wherein the biodegradable polymer comprises a polyanhydride polymer.

The term "polyanhydride" refers to a polymer that is derived from the condensation of carboxylic acids or carboxylic acid derivatives such that repeating units of the resulting polymer are linked by anhydride (—C(=O)—O—C(=O)—) groups. Polyanhydrides can be prepared by condensing diacids or by condensing anhydride prepolymers, as is known in the art. Polyanhydrides are useful polymers for drug delivery systems because of their biodegradability and biocompatibility. Amphiphilic polyanhydride microspheres (PAMs) are chemically and structurally distinct from other polymer or lipid based particle delivery systems. PAMs are solid, surface-eroding particles that encapsulate small molecules or proteins within the polymer matrix, providing sustained release of drug as the PAM erodes. Their degradation pattern of surface erosion makes them suitable for stable drug release applications.

The term "carboxylic anhydride" refers to a compound that contains an anhydride (—C(=O)—O—C(=O)—) group. A carboxylic anhydride typically contains only one anhydride group per molecule. Carboxylic anhydrides can be formed by the condensation of two carboxylic acids. Carboxylic anhydrides that can be used in conjunction with the methods described herein include bis-alkyl carboxylic anhydrides, bis-aryl carboxylic anhydrides, and mixed anhydrides. Examples include, but are not limited to acetic anhydride, trifluoroacetic anhydride, and benzoic anhydride. Mixed anhydrides can also be employed, such as acetic benzoic anhydride, which is the condensation product of acetic acid and benzoic acid.

Polyanhydride polymers can include anhydride polymers comprising 1,ω-bis(carboxy)($C_2$-$C_{10}$)alkane units, preferably 1,ω-bis(carboxy)($C_3$-$C_{10}$)alkane units such as sebacic anhydride, or 1,ω-bis(carboxyphenoxy)($C_2$-$C_{10}$)alkane units, such as 1,3-bis(p-carboxyphenoxy)propane (CPP), 1,6-bis-(p-carboxy-phenoxy)hexane (CPH), or 1,8-bis(carboxyphenoxy)-3,6-dioxaoctane (CPTEG), or combinations thereof.

They may also comprise copolymers comprising 1,ω-bis(carboxy)($C_2$-$C_{10}$)alkane units and 1,ω-bis(carboxyphenoxy)($C_2$-$C_{10}$)alkane units, such as copolymers derived from copolymerization of sebacic anhydride and CPP, CPH and/or CPTEG. The ratio of 1,ω-bis(carboxy)($C_2$-$C_{10}$)alkane to 1,ω-bis(4-carboxyphenoxy)($C_2$-$C_{10}$)alkane units in the microsphere can be about 90:10 to about 50:50 to about 10:90, or any ratio in between, such as 85:15, 80:20, 75:25, 70:30, 60:40, or 55:45, or the reverse of such ratios.

The microspheres may comprise a single polylactide or polylactide-co-glycolide or polyanhydride, or they may comprise mixtures thereof, such as a mixture of two different polymers in the same class, such as a mixture of two different polylactides (e.g. a mixture of poly(D,L-lactide) and poly(L-lactide), or two different polylactide-co-glycolides, or a mixture of two different polyanhydrides, or a mixture of a polylactide and a polylactide-co-glycolide, or a mixture of a polylactide and a polyanhydride, or a mixture of a polylactide-co-glycolide and a polyanhydride.

The percentage of biodegradable polymer may be from about 50% to about 95% w/w of each microsphere, from about 55% to about 90% w/w of each microsphere, from about 60% to about 85% w/w of each microsphere, from about 65% to about 80% w/w of each microsphere, or from about 60% to about 70% w/w of each microsphere.

Cellulose-Derived Material

The composition comprises microspheres comprising a biodegradable polymer, an active ingredient, and a cellulose-derived material (CDM) wherein the percentage of CDM is from about 0.5% to about 6% w/w of each microsphere. The CDM includes cellulose ethers or cellulose esters.

Cellulose ethers include ethyl cellulose, hydroxypropyl cellulose, hydroxypropyl methyl cellulose, and microcrystalline cellulose. Cellulose esters include cellulose acetate, cellulose acetate phthalate, and hydroxypropyl methyl cellulose phthalate. Preferably compositions of the present disclosure comprise ethyl cellulose, carboxymethyl cellulose, hydroxypropylmethyl cellulose, sodium carboxymethyl cellulose, or variations or combinations thereof. More preferably, the compositions comprise ethyl cellulose.

Cellulose ethers such as ethyl cellulose do not occur naturally and are synthetically produced by heating cellulose with caustic solution (e.g. a solution of sodium hydroxide) and treating it an alkyl halide. In the substitution reaction that follows, the hydroxyl residues (—OH functional groups) are replaced by alkoxide (—OR groups). Different kinds of ethyl cellulose can be prepared depending on the number of hydroxyl groups substituted. Cellulose is a polymer consisting of numerous linked glucose molecules, each of which exposes three hydroxyl groups. The Degree of Substitution (DS) of a given form of ethyl cellulose is defined as the average number of substituted hydroxyl groups per glucose. The theoretical maximum is thus a DS of 3.0, however more typical values are 1.3-2.6, corresponding to 43 to 87% of available hydroxyl groups substituted, preferably 44 to 51%, or 48 to 50%. Ethyl cellulose preparations can also differ in the average length of their polymer backbones, which relates both to molecular weight and viscosity. Cellulose esters can be prepared similarly, except the cellulose is treated with acid derivatives such as acid chlorides or anhydrides.

Ethyl cellulose compositions can be characterized by the kinematic viscosity of a standard solution of the polymer. The viscosity of a fluid is a measure of its resistance to gradual deformation by shear stress or tensile stress. For liquids, it corresponds to the informal concept of "thickness"; for example, honey has a much higher viscosity than water. The dynamic (shear) viscosity of a fluid expresses its resistance to shearing flows, where adjacent layers move parallel to each other with different speeds. The kinematic viscosity (also called "momentum diffusivity") is the ratio of the dynamic viscosity μ to the density of the fluid. The term "viscosity grade" with regard to ethyl cellulose arises from the measurement (ASTM D914) of the viscosity of a 5% solution of the polymer in 80:20 toluene/ethanol. Higher viscosity grades correspond generally to higher polymer molecular weight. Ethyl cellulose viscosity grades range from about 3 to about 110 cP, preferably from a lower limit of 4, 10, 20, 40 or 50 cP to an upper limit of 25, 40, 50 or 100 cP.

Compositions described herein include those wherein the cellulose-derived material (CDM) comprises a viscosity fraction of about 0.1% to about 5%; wherein the viscosity fraction is calculated according to the equation $$vf\_CDM = \eta\_inh\_CDM*(f\_CDM)/[\eta\_inh\_CDM*(f\_CDM)+\eta\_inh\_Pol*(f\_Pol)]*100 \quad \text{(Eq. 1)}$$

wherein vf_CDM=the viscosity fraction of CDM in the polymer matrix; η_inh_CDM=the inherent viscosity of the CDM; η_inh_Pol=the inherent viscosity of the polymer, f_CDM=the fraction of CDM in the polymer matrix; and f_Pol=the fraction of polymer in the polymer matrix. Use of this equation is described in more detail in Example 1 for the specific cellulose-derived material ethyl cellulose.

Notable embodiments include those wherein the CDM, such as ethyl cellulose, comprises a viscosity fraction of about 0.1% to about 5%; about 0.5% to about 3.5%; about 0.2% to about 2%; about 0.3% to about 1%; or about 0.5% to about 2%.

In preferred embodiments, at least 90% of the plurality of microspheres have particle diameters from about 40 μm to about 70 μm, from about 45 μm to about 65 μm, from about 50 μm to about 60 μm, from about 50 μm to about 70 μm, from about 40 μm to about 55 μm, from about 60 μm to about 100 μm, from about 65 μm to about 95 μm, from about 70 μm to about 90 μm, from about 70 μm to about 85 μm, from about 70 μm to about 80 μm, or from about 75 μm to about 85 μm.

Other water-insoluble materials included in the matrix of the microspheres in the compositions may comprise waxes, fatty acids or derivatives thereof such as esters or salts, lipids, or combinations or variations thereof. Waxes include any wax-like material suitable for use with the active ingredient. Examples of suitable waxes include, but are not limited to, ceresine wax, beeswax, ozokerite, microcrystalline wax, candelilla wax, montan wax, carnauba wax, paraffin wax, cauassu wax, Japan wax, and Shellac wax. Suitable lipid materials are generally solid at room temperature and may have a melting temperature at or above about 45° C. Examples of suitable lipid materials include, but are not limited to, glycerol fatty acid esters, such as triacylglycerols (e.g., tripalmitin, tristearin, glyceryl trilaurate, coconut oil), hydrogenated fats, ceramides, and organic esters from and/or derived from plants, animals, or minerals.

Examples of suitable fatty acids or derivatives thereof include but are not limited to, stearic acid, sodium stearate, magnesium stearate, glyceryl monostearate, cremophor (castor oil), oleic acid, sodium oleate, lauric acid, sodium laurate, myristic acid, sodium myristate, vegetable oils, coconut oil, mono-, di-, tri-glycerides, stearyl alcohol, and sorbitan esters such as sorbitan monolaurate (Span 20) or sorbitan monooleated (Span 80). For example, in certain embodiments, the fatty acid may be a combination of stearic acid and glyceryl mono stearate.

Therapeutic Agents

The PLA-, PLGA-based and/or polyanhydride-based microspheres of this invention can be loaded with virtually any pharmacologically active substance in order to administer the pharmacologically active substance, i.e. a therapeutic agent or a diagnostic agent, to a subject such as a mammal, including a human subject. The microspheres described herein provide for sustained release of a therapeutic agent as the microsphere erodes, for example within a subject requiring treatment, or within a target parasite in the case of antiparasitic compositions.

The microsphere composition includes those wherein the percentage of active therapeutic agent is from about 10% to about 40% w/w of each microsphere.

Notable compositions include those wherein the active therapeutic agent is an integrase inhibitor, an antiparasitic, a steroid hormone a somatostatin analogue a peptide; and/or wherein the active therapeutic agent is an organic compound having a molecular weight of less than 1000 daltons.

Integrase inhibitors, also known as integrase strand transfer inhibitors (INSTIs), are a class of antiretroviral drug designed to block the action of integrase, a viral enzyme that inserts the viral genome into the DNA of the host cell. Since integration is a vital step in retroviral replication, blocking it can halt further spread of the virus. Integrase inhibitors were initially developed for the treatment of HIV infection, but they could be applied to other retroviruses. Since integrase inhibitors target a distinct step in the retroviral life cycle, they may be taken in combination with other types of HIV drugs to minimize adaptation by the virus. They are also useful in salvage therapy for patients whose virus has mutated and acquired resistance to other drugs. Example integrase inhibitors include dolutegravir, elvitegravir, raltegravir, BI 224436, bictegravir (GS-9883), cabotegravir and MK-2048.

Antiparasitics are a class of medications which are indicated for the treatment of parasitic diseases, such as those caused by helminths, amoebas, ectoparasites, parasitic fungi, and protozoa, among others. Antiparasitics target the parasitic agents of the infections by destroying them or inhibiting their growth; they are usually effective against a limited number of parasites within a particular class. Broad-spectrum antiparasitics, analogous to broad-spectrum antibiotics for bacteria, are antiparasitic drugs with efficacy in treating a wide range of parasitic infections caused by parasites from different classes. Example antiparasitics include the broad spectrum antiparasitic nitazoxanide; antiprotozoals such as melarsoprol and eflornithine (for treatment of sleeping sickness caused by *Trypanosoma brucei*), metronidazole (for vaginitis caused by *Trichomonas*), Tinidazole (for intestinal infections caused by *Giardia lamblia*), and miltefosine (for the treatment of visceral and cutaneous leishmaniasis, and currently undergoing investigation for Chagas disease); antinematodes such as mebendazole and pyrantel pamoate (for most nematode infections; thiabendazole (for roundworm infections); diethylcarbamazine (for treatment of Lymphatic filariasis) and ivermectin (for prevention of river blindness); anticestodes such as albendazole (broad spectrum), niclosamide and praziquantel (for tapeworm infections); antiamoebics such as rifampin and amphotericin B; and antifungals such as fumagillin (for microsporidiosis).

Antiparasitic and/or antimicrobial compounds can be encapsulated into the microspheres, thereby allowing the compounds to be slowly released after they are internalized by parasites as the particles degrade. The ability of the PAMs to slowly erode and release the cargo molecules in a controlled manner allows for specificity against both adult nematodes and the symbiotic bacteria *Wolbachia*. The microspheres can degrade by bulk erosion or surface erosion in the presence of the parasite over a period of time to release the active agents from the interior of the microspheres, thereby killing the parasite or inhibiting the reproduction of the parasite. Administration of the microspheres described herein can therefore interrupt the life cycle of the nematode not by just reducing microfilaria load, but by directly increasing mortality in the adult population.

A steroid hormone is a steroid that acts as a hormone. Steroid hormones can be grouped into two classes: corticosteroids and sex steroids divided into types according to the receptors to which they bind: glucocorticoids, mineralocorticoids (corticosteroids), androgens, estrogens, and progestogens (sex steroids). Vitamin D derivatives are a sixth closely related hormone system with homologous receptors. They have some of the characteristics of true steroids as receptor ligands. Steroid hormones help control metabolism, inflammation, immune functions, salt and water balance, development of sexual characteristics, and the ability to withstand illness and injury. The term steroid describes both hormones produced by the body and artificially produced medications that duplicate the action for the naturally occurring steroids. Synthetic steroids and sterols have also been contrived. Most are steroids, but some non-steroidal molecules can interact with the steroid receptors because of a similarity of shape. Examples of synthetic steroid hormones include glucocorticoids such as alclometasone, prednisone, dexamethasone, triamcinolone, and cortisone; mineralocorticoids such as fludrocortisone; vitamin D analogs such as dihydrotachysterol; androgens (also known as anabolic-androgenic steroids or anabolic steroids) such as oxandrolone, oxabolone, testosterone, and nandrolone; estrogens such as diethylstilbestrol (DES) and estradiol; and progestins such as norethisterone, medroxyprogesterone acetate, etonogestrel and hydroxyprogesterone caproate.

Somatostatin analogs are used for treatment of tumors secreting vasoactive intestinal peptide, carcinoid tumors, glucagonomas and various pituitary adenomas. They are also used to treat acromegaly (a condition in where there is oversecretion of growth hormone in an adult). Representative somatostatin analogs include octreotide, pasireotide, lanreotide and veldoreotide (COR-005).

Pharmaceutical Compositions

The pharmaceutical compositions of the invention include a microsphere or composition described herein, a therapeutic agent as an active ingredient and optionally, a pharmaceutically acceptable carrier and/or excipient or diluent such as a solvent.

Solvents that are applicable to the present disclosure include those used in parenteral drug formulation, including, but not limited to: Class II solvents such as acetonitrile, chloroform, dichloromethane, hexane, methanol, tetrahydrofuran, toluene, and xylene; and Class III solvents such as acetone, butyl acetate, ethanol, dimethyl sulfoxide, and ethyl acetate.

The drug delivery systems or devices or pharmaceutical compositions of this invention encompass compositions made by admixing a microsphere or composition of this invention comprising a therapeutic agent and optionally a pharmaceutically acceptable carrier and/or excipient or diluent. Such compositions are suitable for pharmaceutical use in an animal or human subject.

In some embodiments, this invention provides a pharmaceutical composition including a microsphere described herein, and optionally a pharmaceutically acceptable carrier and/or excipient. The polymers described herein can be combined with a cellulose-derived material and a therapeutic agent in intimate admixture in microspheres described herein, optionally with a suitable pharmaceutical carrier and/or excipient according to conventional pharmaceutical compounding techniques. In some embodiments, this invention provides a pharmaceutical composition including a microsphere described herein, a further therapeutic agent and optionally a pharmaceutically acceptable carrier and/or excipient. The further therapeutic agent is not contained within the microsphere to provide, for example, compositions with both an immediate release of a therapeutic agent and a sustained release of a therapeutic agent. The further therapeutic agent may be the same as or different from the therapeutic agent contained in the microsphere. Any carrier and/or excipient suitable for the form of preparation desired for administration is contemplated for use with the microspheres disclosed herein. The compositions may be prepared by any of the methods well-known in the art of pharmacy.

In some of these embodiments, the pharmaceutically acceptable excipient includes a salt or a diluent.

In some embodiments, the composition is formulated for parenteral (such as intravenous) administration or oral administration and includes the composition and at least one member selected from the group consisting of an aqueous solution and a buffer solution.

In some embodiments, this invention provides compositions further including a pharmaceutical surfactant.

In some embodiments, this invention provides compositions further including a cationic surfactant selected from the group consisting of benzalkonium chloride, benzethonium chloride, and cetrimide.

In some embodiments, this invention provides compositions further including an anionic surfactant selected from the group consisting of docusate sodium and sodium lauryl sulfate.

In some embodiments, this invention provides compositions further including a non-ionic surfactant selected from the group consisting of glyceryl monooleate, sorbitan esters, polyoxyethylene sorbitan fatty acid esters, and polyoxyethylene alkyl ethers. In some embodiments, the non-ionic surfactant is a sorbitan ester selected from the group consisting of sorbitan monolaurate, sorbitan monooleate, sorbitan monopalmitate, sorbitan sesquioleate, and sorbitan trioleate. In some embodiments, the non-ionic surfactant is a polyoxyethylene sorbitan fatty acid ester selected from the group consisting of polysorbate 20, polysorbate 40, polysorbate 60, polysorbate 65, polysorbate 80, and polysorbate 85. In some other embodiments, the non-ionic surfactant is a polyoxyethylene alkyl ether selected from the group consisting of polyethylene glycol monocetyl ether, polyethylene glycol monolauryl ether, polyethylene glycolmonooleyl ether, and polyethylene glycol monostearyl ether. In some embodiments, the poloxamer is selected from the group consisting of P124, P188, P237, P338, and P407.

In some embodiments, this invention provides compositions further comprising a cryoprotectant. In some embodiments, the cryoprotectant is selected from the group consisting of glucose, sucrose, trehalose, lactose, sodium glutamate, PVP, HPβCD, CD, glycerol, maltose, mannitol, and saccharose.

Administration of an appropriate amount of the pharmaceutical composition may be by any means known in the art. The pharmaceutical compositions include compositions suitable for parenteral, pulmonary, nasal, rectal, topical, or oral administration. The most suitable route of administration in any given case will depend in part on the nature and severity of the conditions being diagnosed. Notably, the compositions are suitable for parenteral (systemic) administration. The compositions may be administered by injection, e.g., via a syringe, subcutaneously, intravenously, intramuscularly, intraperitoneally, subconjunctivally, intravitreally. The administration may include delivery into the synovial space (e.g., for the treatment of arthritis) or intrathecal injection (e.g., for the treatment of brain diseases). Other preferred compositions include compositions suitable for other systemic administration including enteral, oral, rectal, sublingual, or sublabial administration.

The compositions, agents, and microspheres described herein are preferably administered parenterally. Solutions or suspensions of these microspheres can be prepared in water suitably mixed with a surfactant such as the pharmaceutically acceptable surfactants described above. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Injection solutions and suspensions can be prepared from sterile powders, granules, and tablets of the kind described below. Formulations suitable for parenteral administration, such as, for example, by intra-articular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Compositions for systemic administration include, but are not limited to, dry powder compositions consisting of the composition as set forth herein and optionally the powder of a suitable carrier and/or excipient. The compositions and/or drug delivery systems for systemic administration can be represented by, but not limited to, tablets, capsules, caplets, pills, syrups, solutions, and suspensions.

Compositions for pulmonary administration include, but are not limited to, dry powder compositions comprising the powder of a microsphere described herein with a therapeutic agent, and optionally the powder of a suitable carrier and/or lubricant. The compositions for pulmonary administration can be inhaled from any suitable dry powder inhaler device known to a person skilled in the art.

Formulations suitable for oral administration can consist of (a) liquid solutions, suspensions, emulsions, or gels, such as an effective amount of the microsphere dispersed in diluents, such as water, saline or PEG 400; optionally with excipients such as surfactants, cosolvents and the like; and (b) capsules, sachets or tablets, each containing a predetermined amount of the active ingredient, as liquids, solids, granules or gelatin. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers.

In the pharmaceutical compositions of this invention for parenteral (subcutaneous, intramuscular, intravenous), oral, sublingual, local or rectal administration, microspheres as described herein, can be administered to animals and humans in unit dosage forms of administration mixed with conventional pharmaceutical carriers. The appropriate unit forms of administration include oral forms such as tablets, gelatin capsules, powders, granules and solutions or suspensions to be taken orally, sublingual and buccal forms of administration, aerosols, implants, subcutaneous, intramuscular, intravenous, intranasal or intraocular forms of administration and rectal forms of administration.

Kits providing a unit dosage of the pharmaceutical compositions set forth herein are contemplated as within this invention. Kits providing many unit dosages of the compositions set forth herein are contemplated as within this invention. Still further, kits providing several unit dosages of the compositions set forth herein are contemplated as within this invention. In some embodiments, the kits of this invention include a unit dosage of a pharmaceutical compositions set forth herein. In certain embodiments, the kits of this invention include many unit dosages of a pharmaceutical compositions set forth herein. In certain other embodiments, the kits of this invention include a unit dosage of a pharmaceutical composition set forth herein.

Drug delivery devices of the invention comprise powders, microspheres, tablets, gelatin capsules, pills, capsules, caplets, sachets and the like as described herein comprising a microsphere described herein. Drug delivery devices also include shaped articles comprising the microspheres, including for example films, disks or rods. Such shaped articles may be suitable for implantation in a subject's body, such as subcutaneously. Drug delivery devices also include devices configured to deliver one or more unit dosages of a pharmaceutical composition comprising a microsphere described herein. Such devices include for example, syringes, aerosol sprayers, pump sprayers, applicators, or inhalers.

The microspheres described herein provide benefits to pharmaceutical formulations including decreased deviation in mean microsphere diameter during fabrication, improved entrapment efficiency and enhanced hydrophobicity, improved microsphere stability in terms of dissolution behavior and thermal resistance and/or the ability to adjust drug release rate. These benefits are demonstrated in the following Examples.

Decreased Deviation in Mean Microsphere Diameter During Fabrication

Examples 1-5 and 13 illustrate how ethyl cellulose improves monodisperse microsphere size variation during fabrication, especially at high drug loadings. Without ethyl cellulose, the high drug content makes it difficult for droplets to harden and for microspheres to retain a spherical shape during manufacture. It is postulated that the water-insoluble binder intercalates the polymer chains and assists in shape retention. Other technologies cannot achieve tight size distributions easily because particle size distributions used with emulsion processes are broad. Some can make very small particles with low drug loading, but the size distribution at that small size is too broad for the injectate (particles+ injection vehicle) to perform reproducibly in terms of overall viscosity and flowability. Precision particle fabrication technology is unique because it can achieve small particle size. By controlling droplet size, precision particle fabrication technology can predict, and resolve, issues around poor entrapment efficiency that other technologies cannot. Competing formulations exhibit drug burst release for the exact same reasons they get poor loading during manufacturing; lack of control over particle size. With inclusion of ethyl cellulose, the advantages of precision particle fabrication are amplified in terms of maintaining tight size distributions with no drug burst at drug loadings over 30% w/w.

Improved Entrapment Efficiency and Enhanced Hydrophobicity

Examples 2-3 illustrate how ethyl cellulose improves drug entrapment during fabrication at high loadings. Without ethyl cellulose, the polymer matrix will sometimes not maintain the ability to localize drug inside the droplet during hardening, especially if the drug has low solubility in water. It is postulated that the water insoluble material intercalates the polymer chains and assists shape retention and decreased diffusion of the drug from the hardening polymer droplet. In addition, because ethyl cellulose is extremely hydrophobic (i.e. water insoluble), it may act as a barrier to drug escape by occupying less free volume at the discontinuous-continuous (droplet-water) phase interface.

Improved Microsphere Stability in Terms of Dissolution Behaviour and Thermal Resistance Examples 5 and 12 illustrate how ethyl cellulose improves stability of the microsphere product at elevated temperatures. Many controlled release polymers and drugs have recommended storage temperatures of −20° C. or below to prevent degradation. Polymers in particular are subject to slow hydrolysis from moisture in the air, and drugs are subject to degradation by a number of means, including oxidation. With ethyl cellulose, polymers and drugs that both have recommended low storage temperatures can safely be stored at 40° C. and 75% RH for extended periods and exhibit (1) no drug degradation, (2) reproducible dissolution kinetics, and (3) reproducible glass transition temperatures (Tg) of the microspheres, indicating resistance to thermal events. Example 5 suggests that benefits of ethyl cellulose inclusion are advantageous at an ethyl cellulose viscosity fraction of no more than 6%.

Ability to Adjust Drug Release Rate

Examples 6-11 highlight how native ethyl cellulose viscosity has the ability to adjust drug release rate. In some instances, the viscosity of ethyl cellulose will be inversely proportional to release rate of drug just as seen with any controlled release polymer (lower viscosity, or lower molecular weight, will enable faster release rate, and higher viscosity or molecular weight, will enable slower release rate). In other instances, this logical phenomenon may not be observed. Although not limited by theory, it is speculated that the polymer chemistry influences whether logical adjustments in release rate can be achieved in binary systems consisting of ethyl cellulose and another polymer. Examples 6-11 generally indicate that (1) for polymers without a glycolide component, ethyl cellulose viscosity can alter release rate, but not in a logical, inversely proportional manner, and (2) for polymers with a glycolide component, release rate is in fact inversely proportional to ethyl cellulose viscosity.

EXAMPLES

Formulations Used

The following microsphere formulations were manufactured with precision particle fabrication technology described in U.S. Pat. Nos. 6,669,961, 7,309,500, and 7,368,130, all of which are incorporated by reference. This particle fabrication technology highlights the advantages of ethyl cellulose inclusion. Details about each formulation (including polymer type, polymer viscosity, ethyl cellulose viscosity, ethyl cellulose fraction, ethyl cellulose viscosity fraction, and drug loading) are tabulated in Tables 1-13 below. Abbreviations for polymers used are listed in Table A. The commercial source for all PLAs and PLGAs was Evonik Industries, Essen, Germany. The ethylcellulose was sourced from Sigma Aldrich in St. Louis, Mo. The compositional and physical properties for the polymers are contained in the "polymer chemistry, co-block ratio, polymer inherent viscosity" columns in the formulation tables, and the ethyl cellulose grade is contained in the "kinematic viscosity" column in the same formulation tables. Properties for drugs used are listed in Table B.

TABLE A

| Abbreviation | Polymer Chemistry |
| --- | --- |
| P-DLL-G | Poly(D,L-lactide-co-glycolide) |
| P-LL-G | Poly(L-lactide-co-glycolide) |
| P-DLL | Poly(D,L-lactide) |
| P-LL-DLL | Poly(L-lactide-co-D,L-lactide) |
| EC | Ethyl cellulose |

TABLE B

| Drug ID | Drug Name | Classification | Molecular Weight | logP | Water Solubility |
|---|---|---|---|---|---|
| A | Elvitegravir | Integrase inhibitor | 448 Da | 4.67 | <0.003 mg/mL |
| B | — | Antiparasitic | 581 Da | 3.66 | <0.010 mg/mL |
| C | Etonogestrel | Steroid hormone | 324 Da | 3.40 | <0.007 mg/mL |
| D | Octreotide | Somatostatin analogue | 1141 Da | 0.43 | >10 mg/mL |

Particle Size and Photographs

Microsphere size was determined via either microscopy or particle size analyzer. For sizes determined by microscopy, a small (about 2 mg) sample of microspheres was placed on a glass slide and wetted to promote particle dispersion. The slide was placed under a microscope objective and visualized with paired software. The software had been previously calibrated with an external scalebar using multiple magnifications. Particle size was quantified by measuring the diameter of a subset of microspheres with the software algorithms and averaging the measurements. Photographs were taken by creating a still image of the microspheres while on the glass slide. For sizes determined with a particle analyzer, a small sample (about 10 mg) of microspheres was dispersed into an Isotonic solution (about 10 mL). The suspension was placed onto the stage of a Coulter Multisizer M3 fitted with a 560 micrometer aperture. The analyzer software was then used to sample the suspension and create a volume-based curve denoting the distribution of particle sizes within the measurement period, which was typically 30 seconds.

Drug Release Determination

The release of drugs from the microspheres was determined according to the following general procedure.

Figure 5A:
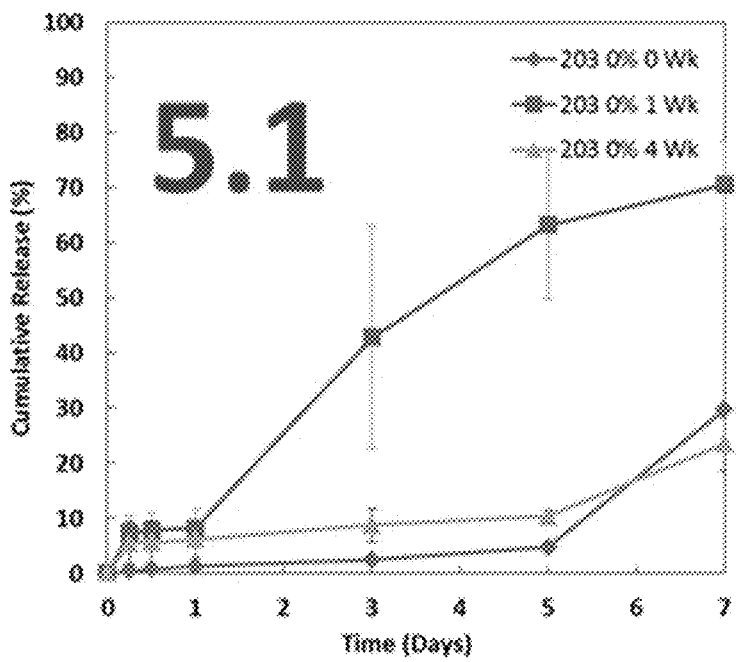
FIGS. 5A to 5F show plots of the cumulative release of the active ingredient from microspheres prepared in Example 5.
Figure 5B:
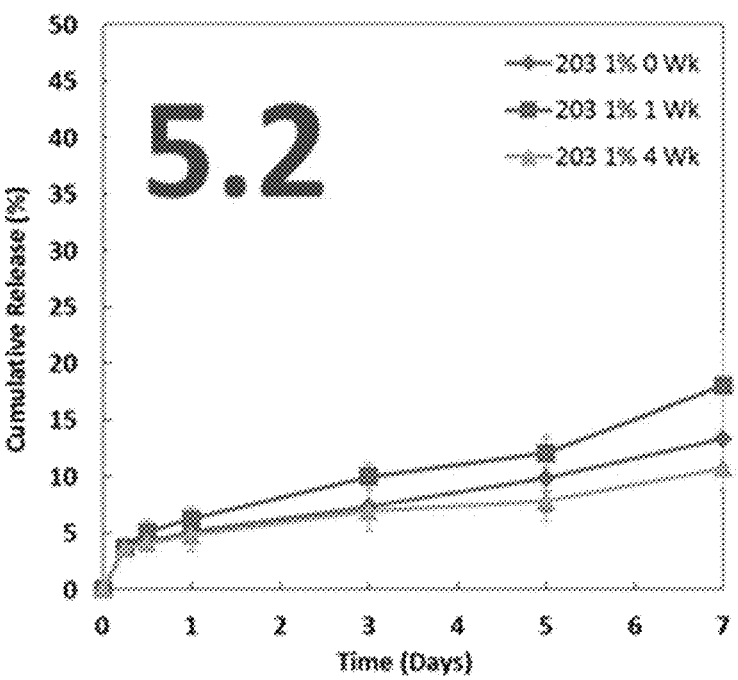
Figure 5C:
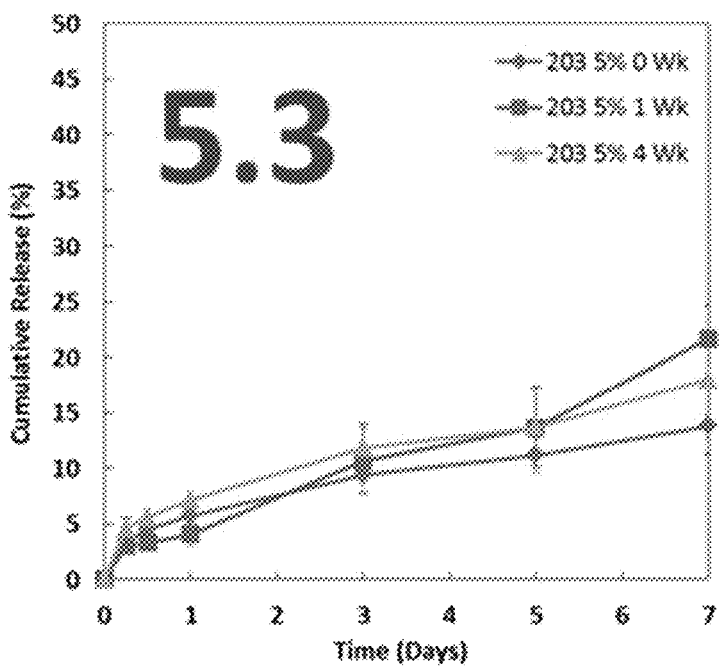
Figure 5D:
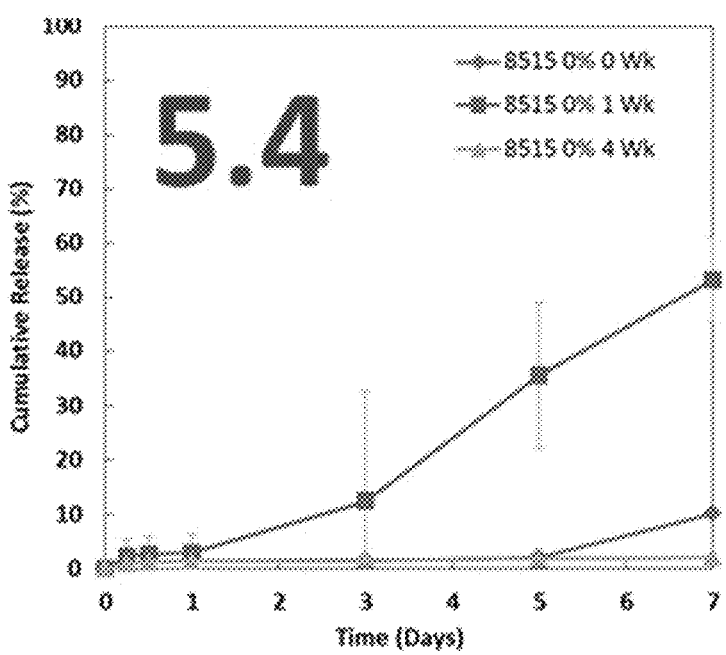
Figure 5E:
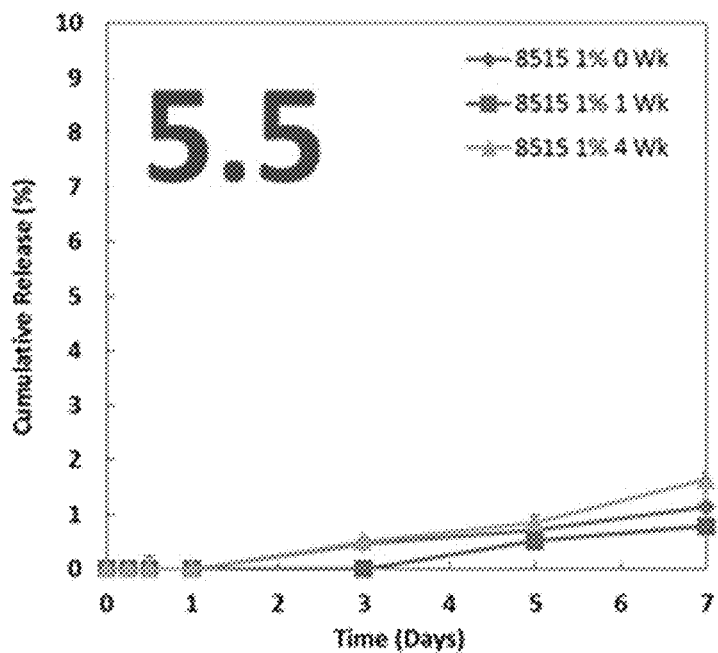
Figure 5F:
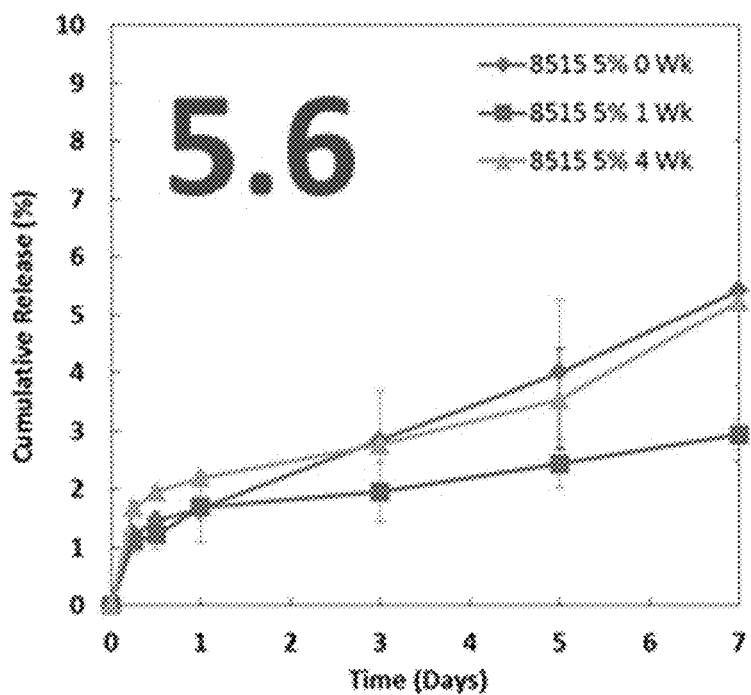

Microspheres containing drug were manufactured according to the pre-determined formulation following the procedures described in Example 1. Following lyophilization, microspheres were divided into samples for dissolution testing at multiple timepoints. For instance, some microspheres were tested immediately upon manufacture (e.g. T=0 Months), and some were stored at ICH temperatures (i.e. 40 degrees centigrade/75% relative humidity) after longer storage periods like T=1 Week, T=4 Weeks/1 month or T=6 months. After storage for the time indicated in the Figures, samples were removed from the incubator, allowed to cool down to room temperature and sampled to determine the release profile. Drug release was quantified by placing a small amount of microspheres (about 10 mg) into a dissolution medium and volume previously determined to provide sink conditions for the active pharmaceutical ingredient. For the active pharmaceutical ingredients (APIs) tested in examples 1-12, the dissolution medium consisted of a 0.1% sodium lauryl sulfate (SLS) solution in either 20 or 60 mL glass scintillation vials at 40 degrees centigrade, with stirbars rotating at 300 rpm. The dissolution medium was sampled at predefined timepoints over several days or months, where after each sampling the medium was refreshed so volume remained constant. Notably the dissolution study for a given sample was conducted over multiple days after removal from storage. For example, a given formulation such as Sample 5.1 (FIG. 5A) was stored for 0 weeks, 1 week or 4 weeks at 40° C., after which samples were removed from the chamber and the dissolution was followed for seven days after removal from storage to provide the cumulative release plots indicated. After each sampling, the dissolution supernatant was filtered and analyzed via high performance liquid chromatography for drug concentration, after which total mass release was calculated by multiplying the concentration by dissolution volume. The mass released at each timepoint was then normalized to the total mass encapsulated within the microsphere, denoted as cumulative release. Drug content within the microsphere was determined by dissolving a defined mass of microspheres (about 10 mg) in a solvent (about 10 mL), and analyzing the content of that extracted sample.

Example 1

Monodisperse microspheres without ethyl cellulose were fabricated from a proprietary process previously described. Briefly, raw poly(D,L-lactide-co-glycolide) (P-DLL-G) 65:35 was added to dichloromethane (DCM) at a concentration of 7% w/v in a 20 mL glass scintillation vial and vortexed until dissolved. Drug A was then co-dissolved with the polymer solution at 3% w/v, bringing the total solids content in the vial to 10% w/v and the theoretical drug loading to 30% w/w. The polymer solution was then loaded into a plastic luer-lock syringe which is affixed to a precision syringe pump, and connected to the custom particle fabrication nozzle with small volume PTFE tubing. The polymer solution was flowed at a rate of 5 mL/hr through the nozzle, which was excited at a 4 kHz frequency via vibratory mechanism. The droplets, which were typically around 20-30 μm in diameter, fell into a 2000 mL glass beaker of deionized (DI) water supplemented with 0.5% w/v poly (vinyl alcohol) (PVA), which served as a surfactant and prevented droplet aggregation. Following ejection of the entire syringe contents, the droplets were stirred at 75 rpm for 3 hours with a stir bar that spans the diameter of the beaker to aid in extraction of the DCM into the PVA solution. Following solvent extraction, stirring was halted, the stir bar was removed with a magnetic wand, and the particles were allowed to settle to the beaker floor, which was completed in 10 minutes. The Water/PVA/DCM supernatant was then removed with a glass pipet and disposed of in an appropriate waste container, and the remaining particles were washed with DI water once before being concentrated into a 50 mL centrifuge tube. The wetted particles were placed in a −80° C. freezer until frozen, and then transferred to a lyophilization chamber at 0.028±0.002 bar and −50±2° C. for 48 hours. When dry, the particle vials were lightly agitated by hand to ensure a flowable powder. Drug content was determined by dissolving dried microsphere samples (about 10 mg) in DCM and quantifying on a high performance liquid chromatography (HPLC) system outfitted with a C18 column. Actual drug content following analysis was found to be 29.4%, making the actual polymer content 70.6%. A small sample was taken from the microsphere powder to obtain microscope images and size distribution with a Coulter Multisizer M3 (Sample 1.1 in FIG. 1A).

Figure 1B:
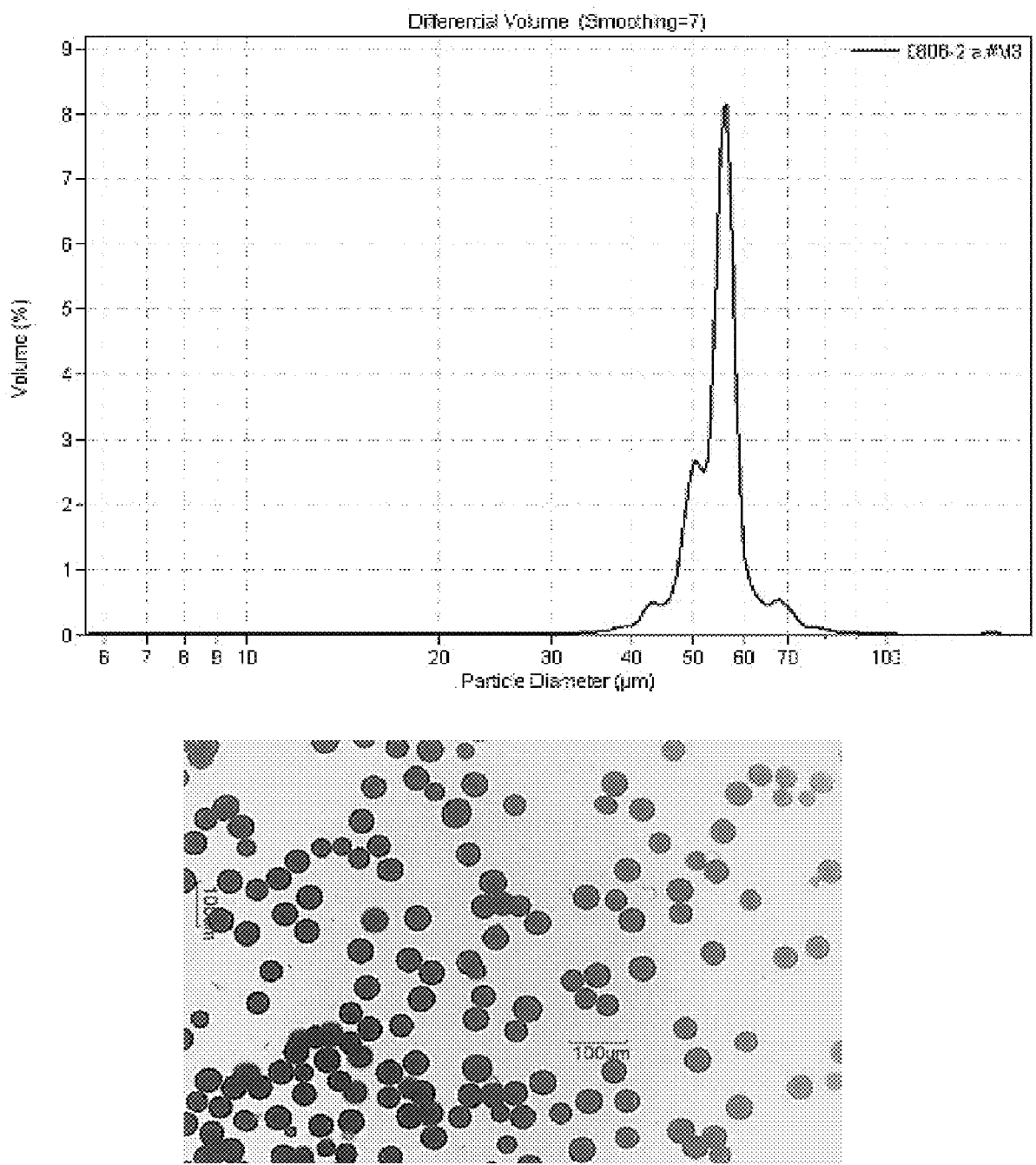
Figure 1C:
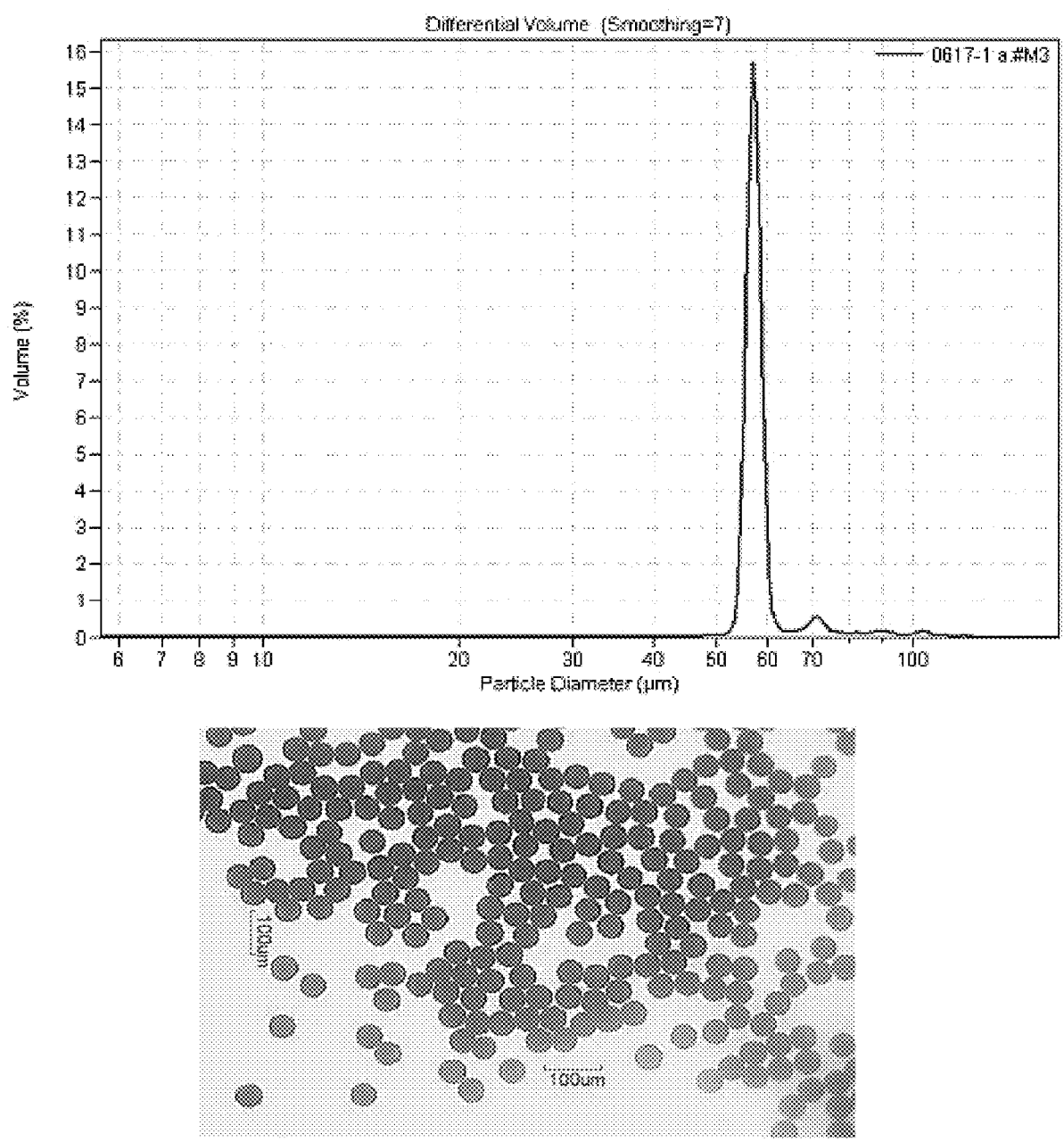

Monodisperse microspheres with ethyl cellulose were fabricated in the manner previously described, only with ethyl cellulose dissolved in the polymer solution such that the theoretical drug loading was 30% w/w, the ethyl cellulose content was 1% w/w, and the polymer content was 69% w/w. Drug content was determined by dissolving dried microsphere samples (about 10 mg) in DCM and quantifying on a high performance liquid chromatography (HPLC) system outfitted with a C18 column. Actual drug content following analysis was found to be 29.4%, making the actual polymer and ethyl cellulose content 69.6% and 1.0%, respectively. A small sample was taken from the microsphere powder to obtain microscope images and size distribution with a Coulter Multisizer M3 (Sample 1.3 in FIG. 1C).

The content of ethyl cellulose in the controlled release matrix can be denoted as the inherent viscosity fraction, where the inherent viscosity fraction consists of a weighted average of the polymer inherent viscosity and the ethyl cellulose inherent viscosity fraction. Simply, the viscosity fraction is the contribution of ethyl cellulose to the overall viscosity of the controlled release matrix during microsphere synthesis. Often, the viscosity of ethyl cellulose is reported as solution viscosity, not as inherent viscosity, and it must be converted before being weighted with the polymer inherent viscosity. In Sample 1.3, ethyl cellulose was said to have a viscosity of 22 cP in a 5% w/v 80:20 toluene:ethanol solution (i.e. its viscosity grade), and P-DLL-G was said to have an average viscosity of 0.4 dL/g. They are combined in a microsphere such that the whole particle formulation is comprised of 1.0% w/w ethyl cellulose, 29.4% drug, and 69.6% polymer. Knowing that the viscosity of an 80:20 toluene:ethanol mixture is 0.527 cP, one must calculate the inherent viscosity fraction of the polymer-ethyl cellulose system (not including drug). First, the kinematic viscosity of the ethyl cellulose solution must be converted to inherent viscosity of the ethyl cellulose itself. The inherent viscosity can be calculated using the relation in Equation 2 wherein $\eta\_inh$=the inherent viscosity of the material (in dL/g); $\eta\_solute$=the kinematic viscosity of the solution (in cP); $\eta\_solvent$=the kinematic viscosity of the solvent (in cP); $c\_solution$=the concentration of the solution (in g/dL):

$$\eta\_inh = \ln(\eta\_solution/\eta\_solvent)/c\_solution \quad \text{(Eq. 2)}$$

Accordingly, the inherent viscosity of the ethyl cellulose entity itself is determined to be $\eta\_inh = \ln(22\ cP/0.527\ cP)/5\ g/dL = 0.746$.

Though the absolute ethyl cellulose content is 1.0% w/w with respect to the whole microsphere formulation (EC+Drug+PDLLG), assuming no polymer or ethyl cellulose was lost in fabrication, the fraction of ethyl cellulose with respect to non-drug components is based only on theoretical contribution of those two components. In Sample 1.3, the theoretical composition of EC and polymer were 1.0% and 69% respectively, thus ethyl cellulose is 1.0%/(1.0%+69.0%)*100=1.43% of the controlled release matrix component (EC+PDLLG), with the P-DLL-G constituting the remaining 98.57%. Thus, the viscosity fraction of ethyl cellulose in the controlled release component can be calculated to according to the relationship in Eq. 2, wherein $vf\_EC$=the viscosity fraction of ethyl cellulose in the controlled-release component; $\eta\_inh\_EC$=the inherent viscosity of ethyl cellulose; $\eta\_inh\_PDLLG$=the inherent viscosity of the polymer, P-DLL-G; $f\_EC$=the fraction of ethyl cellulose in the controlled release component; and $f\_PDLLG$=the fraction of polymer (P-DLL-G) in the controlled release component $$vf\_EC = \eta\_inh\_EC*(f\_EC)/[\eta\_inh\_EC*(f\_EC) + \eta\_inh\_PDLLG*(f\_PDLLG)]*100 \quad \text{(Eq. 3)}$$

$$vf\_EC = 0.746\ dL/g*(0.0143)/[0.746\ dL/g*(0.0143) + 0.4\ dL/g*(0.9857)]*100 = 2.63\%,\text{ which is reflected in Table 1 and calculated for subsequent Examples.}$$

Figure 1D:
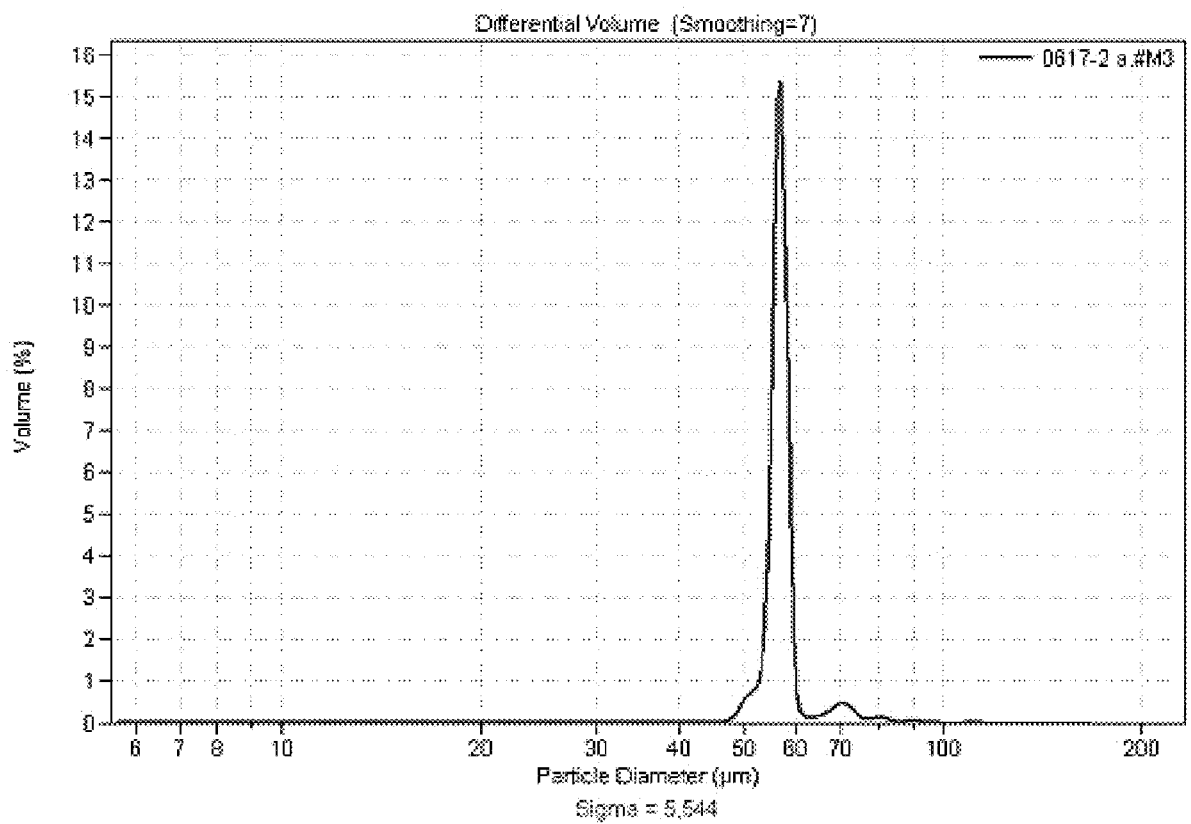
Figure 1D:
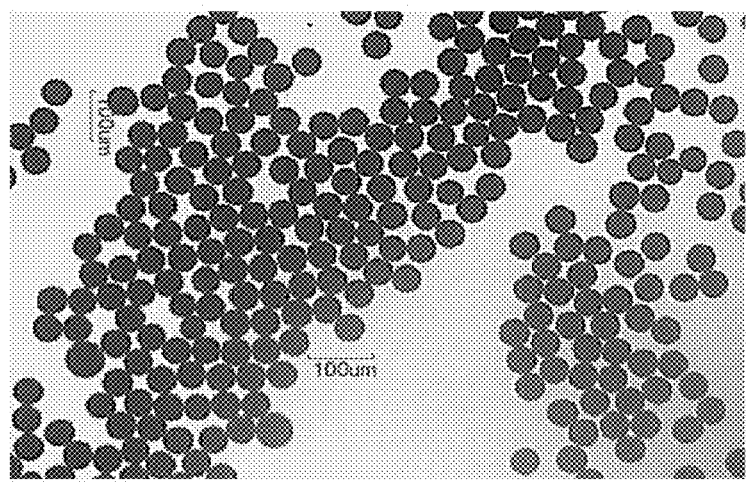
Figure 1E:
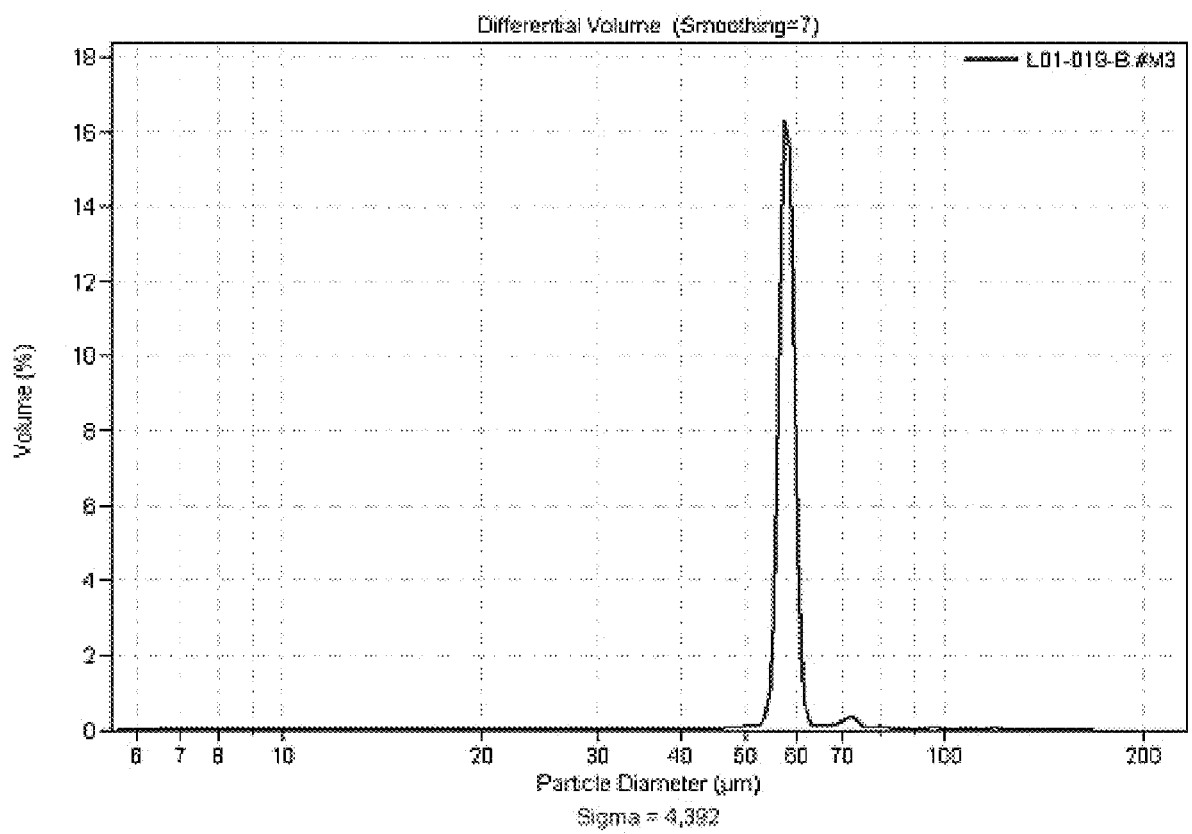
Figure 1E:
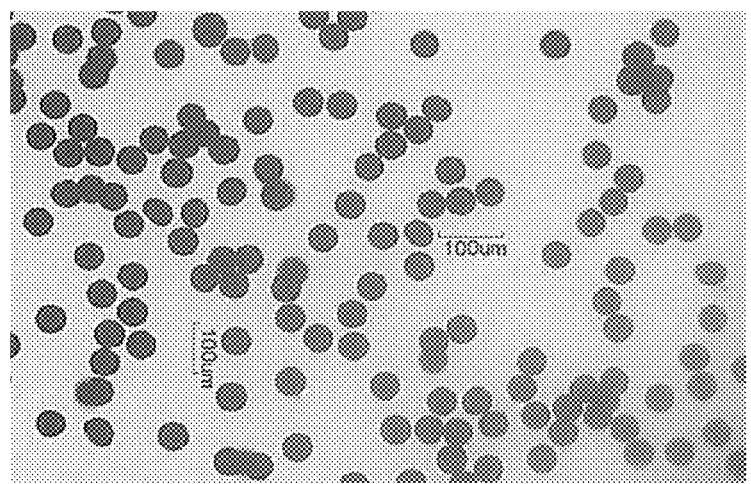

Lastly, monodisperse microspheres with 1% w/w ethyl cellulose and varying drug concentrations were then fabricated in the manner described previously. Drug content was determined by dissolving dried microsphere sample (about 10 mg) in DCM and quantifying on a high performance liquid chromatography (HPLC) system outfitted with a C18 column. Actual drug, polymer, and ethyl cellulose contents are tabulated in Table 1. A small sample was taken from the microsphere powder to obtain microscope images and size distribution with a Coulter Multisizer M3 (Samples 1.2, 1.4-1.5 in FIGS. 1B, 1D and 1E, respectively). Samples 1.1 and 1.2 are EC-free control samples and samples 1.3-1.5 each contain about 1% EC in the formulation.

TABLE 1

|  | Sample ID | | | | |
| --- | --- | --- | --- | --- | --- |
|  | 1.1 | 1.2 | 1.3 | 1.4 | 1.5 |
| Polymer Type | P-DLL-G | P-DLL-G | P-DLL-G | P-DLL-G | P-DLL-G |
| Co-Block Ratios (%-%) | 65-35 | 65-35 | 65-35 | 65-35 | 65-35 |
| Polymer Inherent Viscosity (dL/g) | 0.40 | 0.40 | 0.40 | 0.40 | 0.40 |
| Absolute Polymer Content (% w/w) | 70.60 | 61.49 | 69.57 | 60.26 | 50.11 |
| Relative Polymer Content in Matrix (%) | 100.00 | 100.00 | 98.57 | 98.33 | 98.00 |
| EC Kinematic Viscosity (cP) | — | — | 22 | 22 | 22 |
| EC Inherent Viscosity (dL/g) | — | — | 0.75 | 0.75 | 0.75 |
| Absolute EC Content (% w/w) | — | — | 1.01 | 1.01 | 1.01 |
| Relative EC Content in Matrix (% w/w) | — | — | 1.43 | 1.67 | 2.00 |
| EC Viscosity Fraction (%) | — | — | 2.63 | 3.07 | 3.67 |
| Drug | A | A | A | A | A |
| Absolute Drug Content (% w/w) | 29.40 | 38.51 | 29.42 | 38.73 | 48.88 |
| Toluene:Ethanol 80:20 viscosity (cP) | 0.527 |  |  |  |  |

FIGS. 1A to 1E shows plots of particle size distribution and photomicrographs of microspheres of Samples 1.1 to 1.5, respectively. Data from Samples 1.3-1.5 demonstrate that inclusion of ethyl cellulose improves microsphere droplet formation and decreases deviation in mean microsphere diameter compared to Samples 1.1 and 1.2 that do not include ethyl cellulose.

Example 2

Monodisperse microspheres with and without ethyl cellulose were fabricated as described in Example 1, only with P-DLL-G 85:15 and a 40% theoretical load of Drug B (Samples 2.1-2.2).

TABLE 2

|  | Sample ID | |
| --- | --- | --- |
|  | 2.1 | 2.2 |
| Polymer Type | P-DLL-G | P-DLL-G |
| Co-Block Ratios (%-%) | 85-15 | 85-15 |
| Polymer Inherent Viscosity (dL/g) | 0.70 | 0.70 |
| Absolute Polymer Content (% w/w) | 64.32 | 62.38 |
| Relative Polymer Content in Matrix (%) | 100.00 | 98.33 |
| EC Kinematic Viscosity (cP) | — | 22 |
| EC Inherent Viscosity (dL/g) | — | 0.75 |
| Absolute EC Content (% w/w) | — | 1.04 |
| Relative EC Content in Matrix (% w/w) | — | 1.67 |
| EC Viscosity Fraction (%) | — | 1.77 |
| Drug | B | B |
| Absolute Drug Content (% w/w) | 35.68 | 36.58 |

Figure 2:
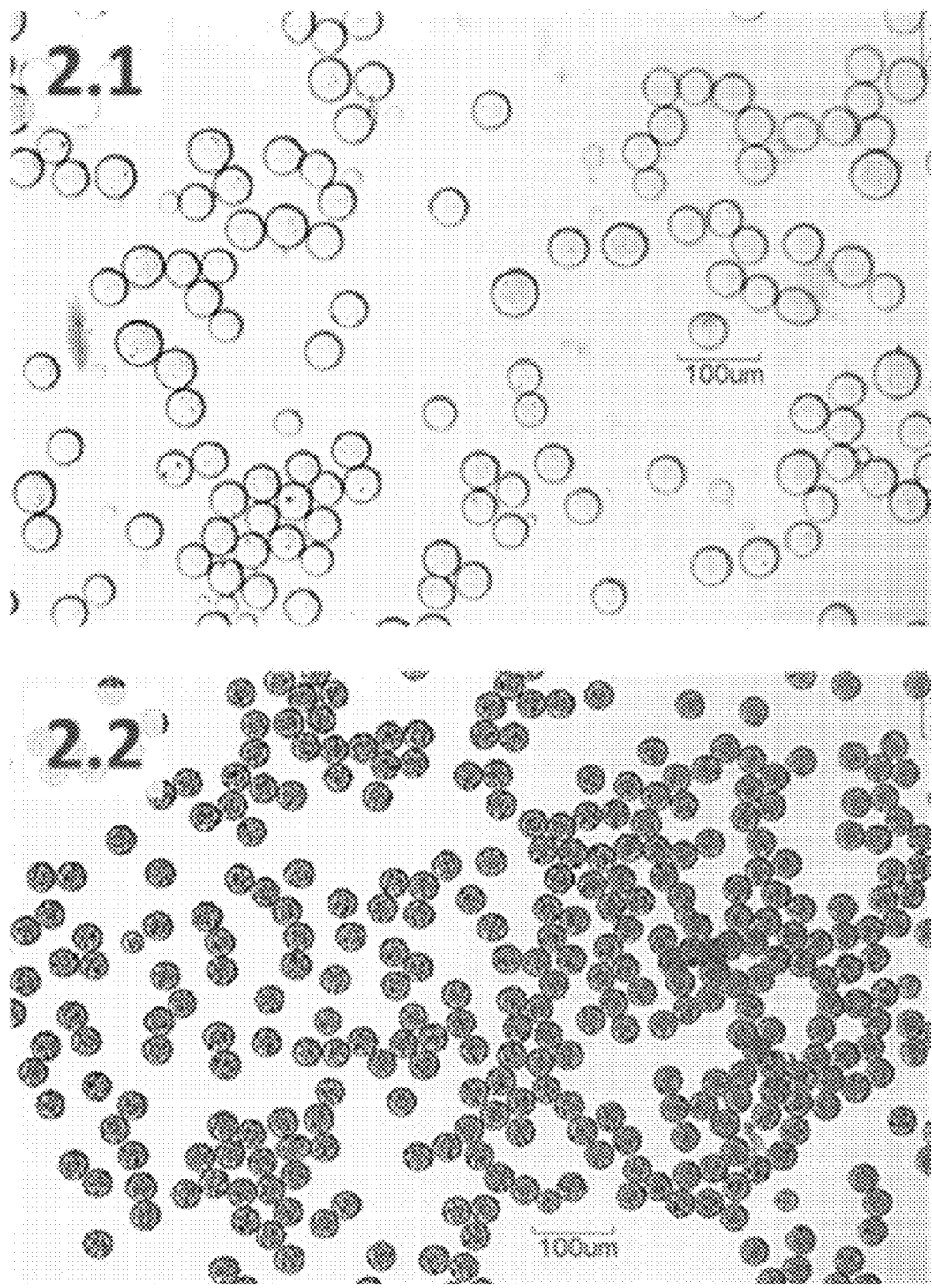
FIG. 2 shows photomicrographs of microspheres prepared in Example 2.

The photographs in FIG. 2 demonstrate that inclusion of ethyl cellulose improves microsphere droplet formation, decreases deviation in mean microsphere diameter, and improved drug entrapment efficiency. Specifically, when ethylcellulose is included, microsphere sphericity is highly predictable (Sample 2.2), whereas without ethylcellulose, some particles are oblong, eccentric, or pill-shaped (Sample 2.1). Additionally, the diameter variation of microspheres without ethylcellulose is much wider and inconsistent compared to particles with ethylcellulose.

Example 3

Monodisperse microspheres with and without ethyl cellulose were fabricated as described in Example 1, only using P-DLL-G 75:25 and a 40% theoretical load of Drug B (Samples 3.1-3.2).

TABLE 3

|  | Sample ID | |
| --- | --- | --- |
|  | 3.1 | 3.2 |
| Polymer Type | P-DLL-G | P-DLL-G |
| Co-Block Ratios (%-%) | 75-25 | 75-25 |
| Polymer Inherent Viscosity (dL/g) | 0.85 | 0.85 |
| Absolute Polymer Content (% w/w) | 68.23 | 60.70 |
| Relative Polymer Content in Matrix (%) | 100.00 | 98.33 |
| EC Kinematic Viscosity (cP) | — | 22 |
| EC Inherent Viscosity (dL/g) | — | 0.75 |
| Absolute EC Content (% w/w) | — | 1.02 |
| Relative EC Content in Matrix (% w/w) | — | 1.67 |
| EC Viscosity Fraction (%) | — | 1.47 |
| Drug | B | B |
| Absolute Drug Content (% w/w) | 31.77 | 38.28 |

Figure 3:
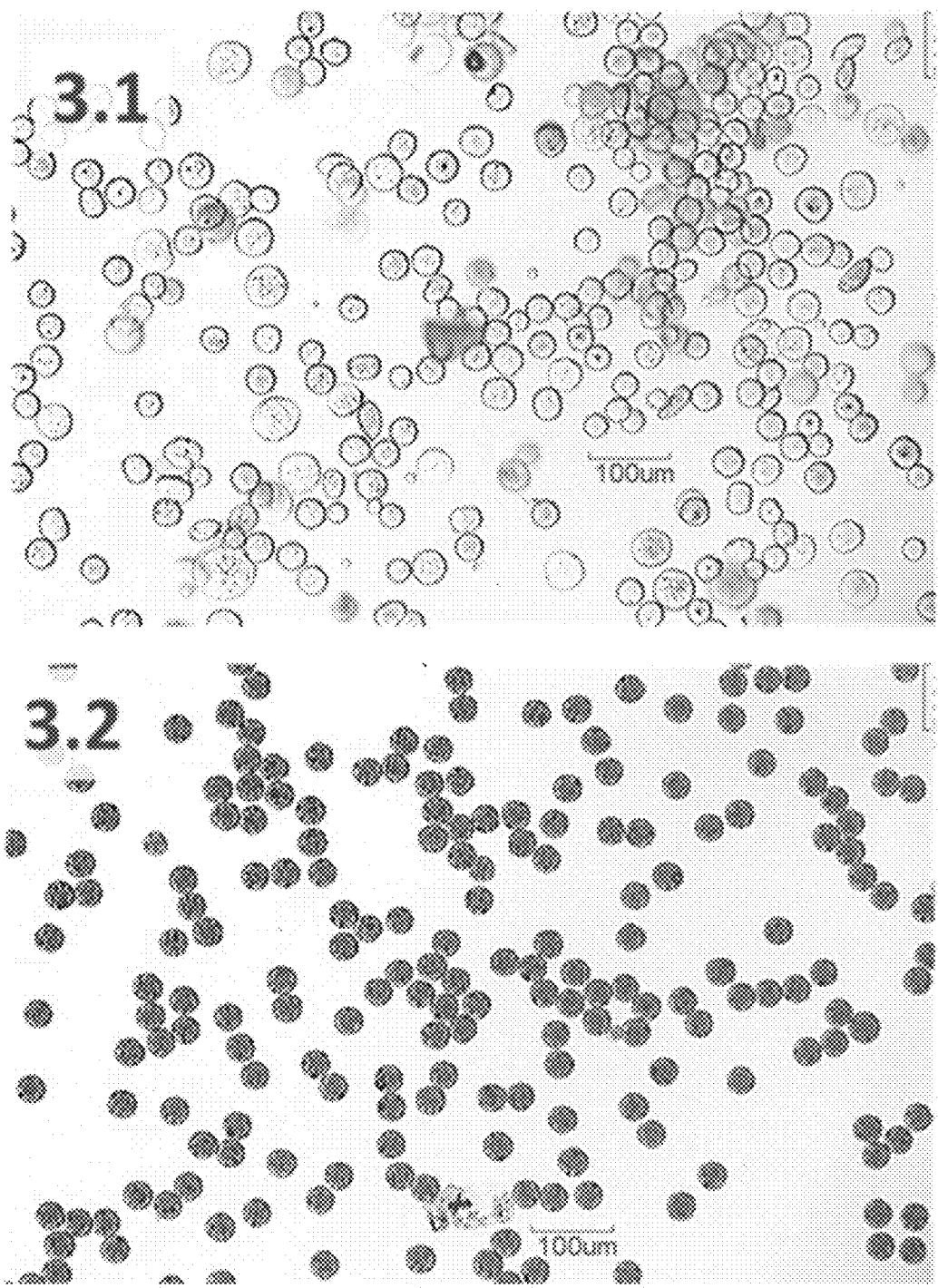
FIG. 3 shows photomicrographs of microspheres prepared in Example 3.
Figure 4:
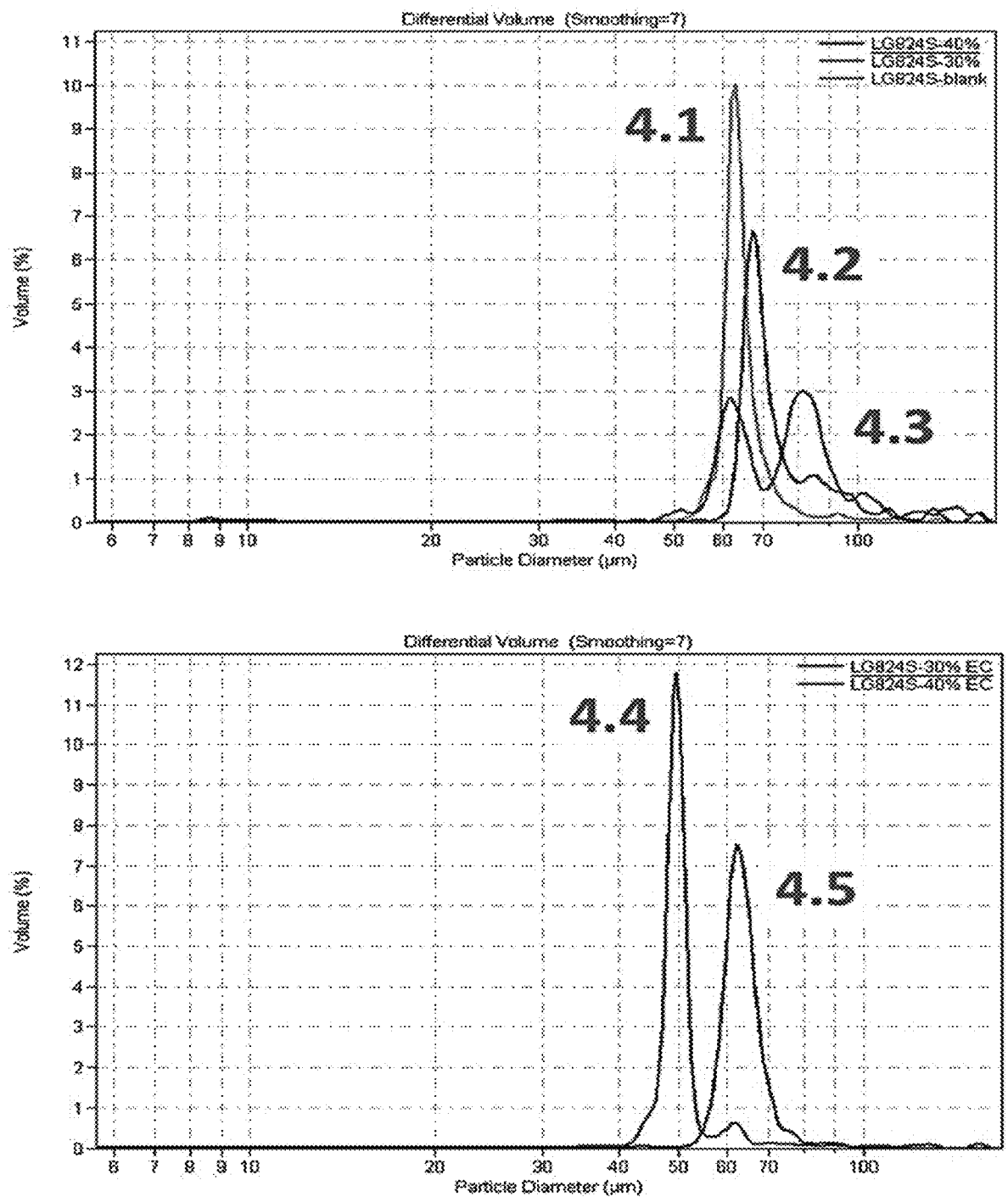
FIG. 4 shows plots of particle size distribution of microspheres prepared in Example 4.

The photographs in FIG. 3 demonstrate that inclusion of ethyl cellulose improves microsphere droplet formation, decreases deviation in mean microsphere diameter, and improved drug entrapment efficiency. When ethylcellulose is included (Sample 3.2), microsphere sphericity is highly predictable, whereas without ethylcellulose (Sample 3.1), some particles are oblong, eccentric, or pill-shaped. Additionally, the diameter variation of microspheres without ethylcellulose is much wider and inconsistent compared to particles with ethylcellulose.

Example 4

Monodisperse microspheres with and without ethyl cellulose were fabricated as described in Example 1, only using poly(L-lactide-co-glycolide) (P-LL-G) 85:15 and varying concentrations of Drug C (Samples 4.1-4.2). 4.1 is a drug-free and EC-free sample, 4.2 and 4.3 are EC-free samples.

TABLE 4

|  | Sample ID | | | | |
| --- | --- | --- | --- | --- | --- |
|  | 4.1 | 4.2 | 4.3 | 4.4 | 4.5 |
| Polymer Type | P-LL-G | P-LL-G | P-LL-G | P-LL-G | P-LL-G |
| Co-Block Ratios (%-%) | 85-15 | 85-15 | 85-15 | 85-15 | 85-15 |
| Polymer Inherent Viscosity (dL/g) | 2.15 | 2.15 | 2.15 | 2.15 | 2.15 |
| Absolute Polymer Content (% w/w) | 100.00 | 71.86 | 67.96 | 70.32 | 59.59 |
| Relative Polymer Content in Matrix (%) | 100.00 | 100.00 | 100.00 | 98.57 | 98.33 |
| EC Kinematic Viscosity (cP) | — | — | — | 22 | 22 |
| EC Inherent Viscosity (dL/g) | — | — | — | 0.75 | 0.75 |
| Absolute EC Content (% w/w) | — | — | — | 1.01 | 1.01 |
| Relative EC Content in Matrix (% w/w) | — | — | — | 1.43 | 1.67 |
| EC Viscosity Fraction (%) | — | — | — | 0.50 | 0.58 |
| Drug | — | C | C | C | C |
| Absolute Drug Content (% w/w) | — | 28.14 | 32.04 | 28.67 | 39.40 |

Data from Samples 4.4-4.5 demonstrate that inclusion of ethyl cellulose improves microsphere droplet formation and decreases deviation in mean microsphere diameter compared to Samples 4.1, 4.2 and 4.3 that do not include ethyl cellulose.

Example 5

Monodisperse microspheres were fabricated as described in Example 1, only using poly(D,L-lactide) (P-DL-G) 100:0 or P-DLL-G 85:15, Drug C, and varying concentrations of ethyl cellulose (Samples 5.1-5.6).

TABLE 5

| Sample ID | 5.1 | 5.2 | 5.3 | 5.4 | 5.5 | 5.6 |
|---|---|---|---|---|---|---|
| Polymer Type | P-DLL | P-DLL | P-DLL | P-DLL-G | P-DLL-G | P-DLL-G |
| Co-Block Ratios (%-%) | 100-0 | 100-0 | 100-0 | 85-15 | 85-15 | 85-15 |
| Polymer Inherent Viscosity (dL/g) | 0.30 | 0.30 | 0.30 | 0.70 | 0.70 | 0.70 |
| Absolute Polymer Content (% w/w) | 81.59 | 81.51 | 78.33 | 81.33 | 79.88 | 75.30 |
| Relative Polymer Content in Matrix (%) | 100.00 | 98.75 | 93.75 | 100.00 | 98.75 | 93.75 |
| EC Kinematic Viscosity (cP) | — | 22 | 22 | — | 22 | 22 |
| EC Inherent Viscosity (dL/g) | — | 0.75 | 0.75 | — | 0.75 | 0.75 |
| Absolute EC Content (% w/w) | — | 1.03 | 5.18 | — | 1.01 | 5.02 |
| Relative EC Content in Matrix (% w/w) | — | 1.25 | 6.25 | — | 1.25 | 6.25 |
| EC Viscosity Fraction (%) | — | 3.05 | 14.23 | — | 1.33 | 6.64 |
| Drug | C | C | C | C | C | C |
| Absolute Drug Content (% w/w) | 18.41 | 17.46 | 16.49 | 18.67 | 19.11 | 19.68 |

FIGS. 5A to 5F show plots of the cumulative release of the active ingredient from microspheres 5.1 to 5.6 respectively, as prepared in Example 5. Samples of each formulation type were stored for 0 weeks, 1 week or 4 weeks at 40° C. (indicated as traces for each of the storage periods). Samples were removed from the chamber after the storage period and the dissolution was followed for seven days after removal from storage to provide the cumulative release plots indicated. The data represented in these Figures demonstrate that inclusion of ethyl cellulose improved microsphere dissolution reproducibility after storage stability testing at 40° C./75% RH in sealed glass vials, but the benefits of which are not present when the ethyl cellulose viscosity fraction is above 5%. Inclusion of ethyl cellulose also reduced the release rate of the drug from the microspheres.

Example 6

Monodisperse microspheres were fabricated as described in Example 1, only using P-DLL 100:0, Drug C, and varying viscosities of ethyl cellulose (Samples 6.1-6.3).

TABLE 6

| | Sample ID | | |
|---|---|---|---|
| | 6.1 | 6.2 | 6.3 |
| Polymer Type | P-DLL | P-DLL | P-DLL |
| Co-Block Ratios (%-%) | 100-0 | 100-0 | 100-0 |
| Polymer Inherent Viscosity (dL/g) | 0.30 | 0.30 | 0.30 |
| Absolute Polymer Content (% w/w) | 81.48 | 82.03 | 80.14 |
| Relative Polymer Content in Matrix (%) | 98.75 | 98.75 | 98.75 |
| EC Kinematic Viscosity (cP) | 4 | 22 | 100 |
| EC Inherent Viscosity (dL/g) | 0.41 | 0.75 | 1.05 |
| Absolute EC Content (% w/w) | 1.03 | 1.03 | 1.01 |
| Relative EC Content in Matrix (% w/w) | 1.25 | 1.25 | 1.25 |
| EC Viscosity Fraction (%) | 1.68 | 3.05 | 4.24 |
| Drug | C | C | C |
| Absolute Drug Content (% w/w) | 17.49 | 16.94 | 18.85 |

Figure 6:
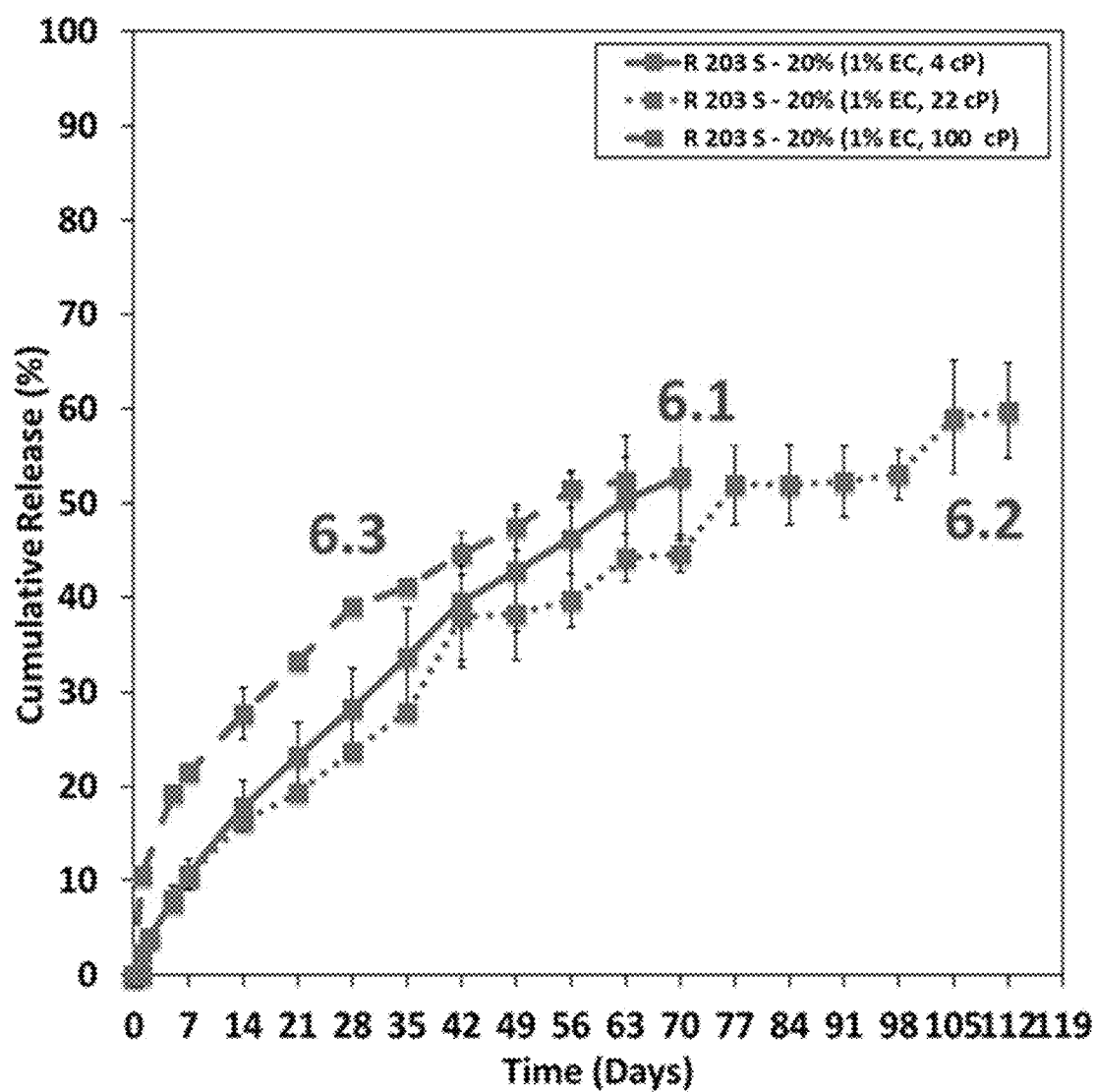
FIG. 6 shows a plot of the cumulative release of the active ingredient from microspheres prepared in Example 6.

The data represented in FIG. 6 demonstrate that inclusion of ethyl cellulose reduced the rate of drug release (compare sample 6.2 to sample 5.1). The viscosity grade of the ethyl cellulose, related to molecular weight as discussed above, also affects release rate of Drug C.

Example 7

Monodisperse microspheres were fabricated as described in Example 1, only using a higher viscosity P-DLL 100:0, Drug C, and varying viscosities of ethyl cellulose (Samples 7.1-7.3).

TABLE 7

| | Sample ID | | |
|---|---|---|---|
| | 7.1 | 7.2 | 7.3 |
| Polymer Type | P-DLL | P-DLL | P-DLL |
| Co-Block Ratios (%-%) | 100-0 | 100-0 | 100-0 |
| Polymer Inherent Viscosity (dL/g) | 1.50 | 1.50 | 1.50 |
| Absolute Polymer Content (% w/w) | 77.95 | 81.07 | 80.93 |
| Relative Polymer Content in Matrix (%) | 98.75 | 98.75 | 98.75 |
| EC Kinematic Viscosity (cP) | 4 | 22 | 100 |
| EC Inherent Viscosity (dL/g) | 0.41 | 0.75 | 1.05 |
| Absolute EC Content (% w/w) | 0.99 | 1.02 | 1.02 |
| Relative EC Content in Matrix (% w/w) | 1.25 | 1.25 | 1.25 |
| EC Viscosity Fraction (%) | 0.34 | 0.63 | 0.88 |
| Drug | C | C | C |
| Absolute Drug Content (% w/w) | 21.06 | 17.91 | 18.05 |

Figure 7:
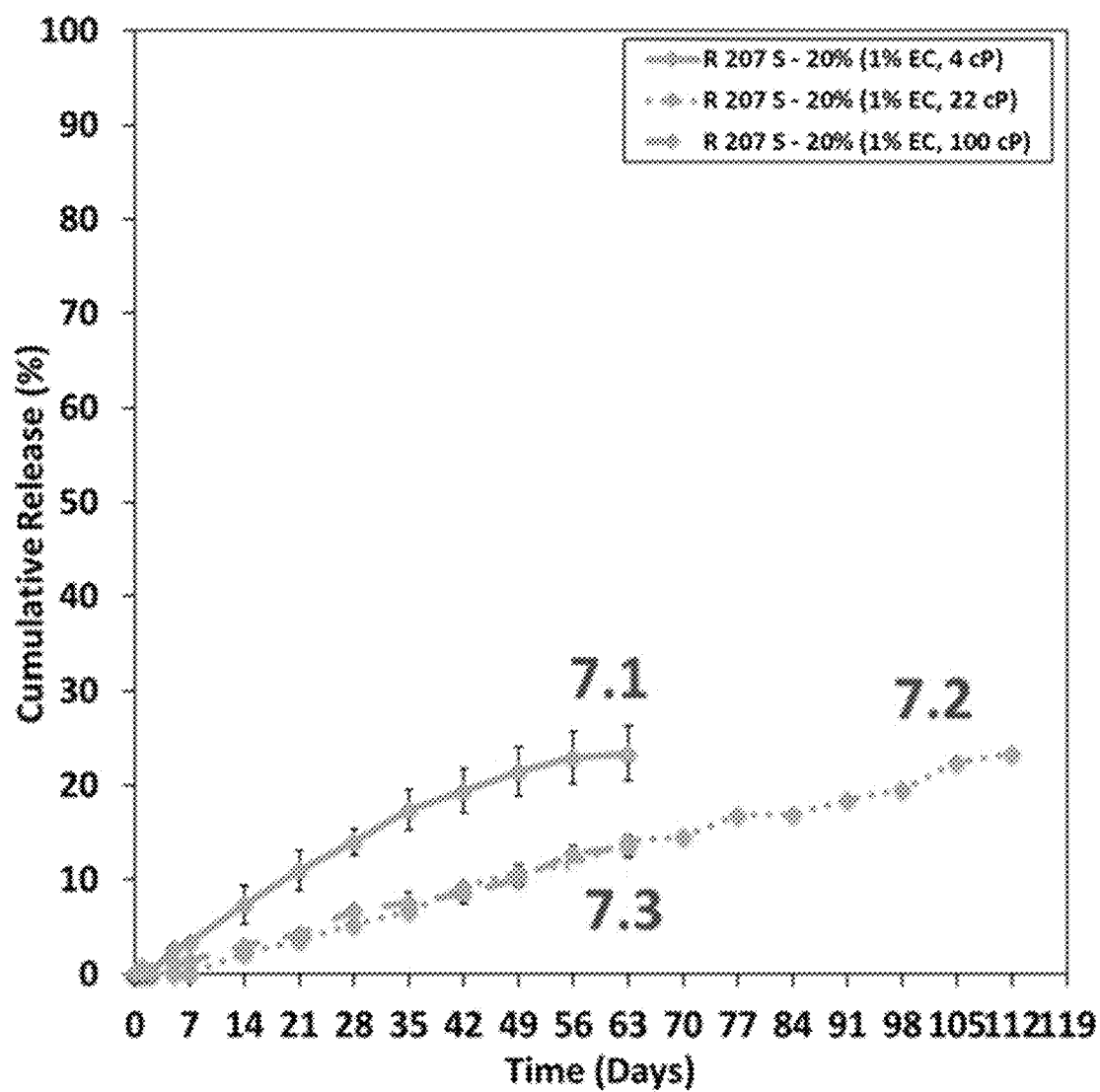
FIG. 7 shows a plot of the cumulative release of the active ingredient from microspheres prepared in Example 7.

The data represented in FIG. 7 demonstrates that the viscosity of ethyl cellulose affects release rate of Drug C.

Example 8

Monodisperse microspheres were fabricated as described in Example 1, only using P-DLL-G 85:15, Drug C, and varying viscosities of ethyl cellulose (Samples 8.1-8.3).

TABLE 8

| | Sample ID | | |
|---|---|---|---|
| | 8.1 | 8.2 | 8.3 |
| Polymer Type | P-DLL-G | P-DLL-G | P-DLL-G |
| Co-Block Ratios (%-%) | 85-15 | 85-15 | 85-15 |
| Polymer Inherent Viscosity (dL/g) | 0.70 | 0.70 | 0.70 |
| Absolute Polymer Content (% w/w) | 78.56 | 79.43 | 80.30 |
| Relative Polymer Content in Matrix (%) | 98.75 | 98.75 | 98.75 |
| EC Kinematic Viscosity (cP) | 4 | 22 | 100 |
| EC Inherent Viscosity (dL/g) | 0.41 | 0.75 | 1.05 |
| Absolute EC Content (% w/w) | 1.00 | 1.00 | 1.01 |
| Relative EC Content in Matrix (% w/w) | 1.25 | 1.25 | 1.25 |
| EC Viscosity Fraction (%) | 0.73 | 1.33 | 1.86 |
| Drug | C | C | C |
| Absolute Drug Content (% w/w) | 20.44 | 19.57 | 18.69 |

Figure 8:
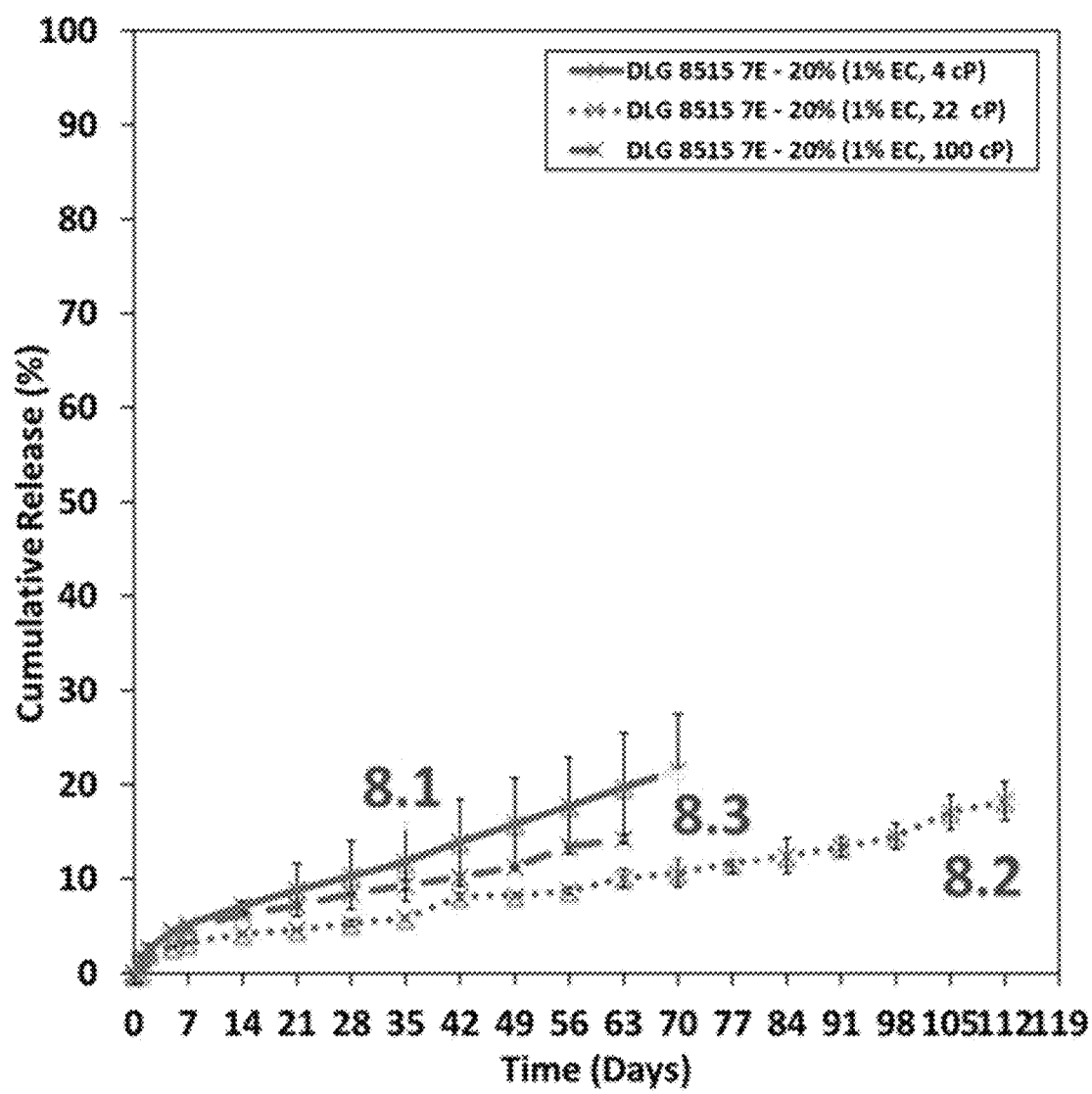
FIG. 8 shows a plot of the cumulative release of the active ingredient from microspheres prepared in Example 8.

The data represented in FIG. 8 demonstrates that the viscosity of ethyl cellulose affects release rate of Drug C.

Example 9

Monodisperse microspheres were fabricated as described in Example 1, only using a higher viscosity P-DLL-G 85:15, Drug C, and varying viscosities of ethyl cellulose (Samples 9.1-9.3).

TABLE 9

| | Sample ID | | |
|---|---|---|---|
| | 9.1 | 9.2 | 9.3 |
| Polymer Type | P-DLL-G | P-DLL-G | P-DLL-G |
| Co-Block Ratios (%-%) | 85-15 | 85-15 | 85-15 |
| Polymer Inherent Viscosity (dL/g) | 1.50 | 1.50 | 1.50 |
| Absolute Polymer Content (% w/w) | 78.39 | 79.64 | 81.27 |
| Relative Polymer Content in Matrix (%) | 98.75 | 98.75 | 98.75 |
| EC Kinematic Viscosity (cP) | 4 | 22 | 100 |
| EC Inherent Viscosity (dL/g) | 0.41 | 0.75 | 1.05 |
| Absolute EC Content (% w/w) | 0.99 | 1.01 | 1.02 |
| Relative EC Content in Matrix (% w/w) | 1.25 | 1.25 | 1.25 |
| EC Viscosity Fraction (%) | 0.34 | 0.63 | 0.88 |
| Drug | C | C | C |
| Absolute Drug Content (% w/w) | 20.62 | 19.35 | 17.71 |

Figure 9:
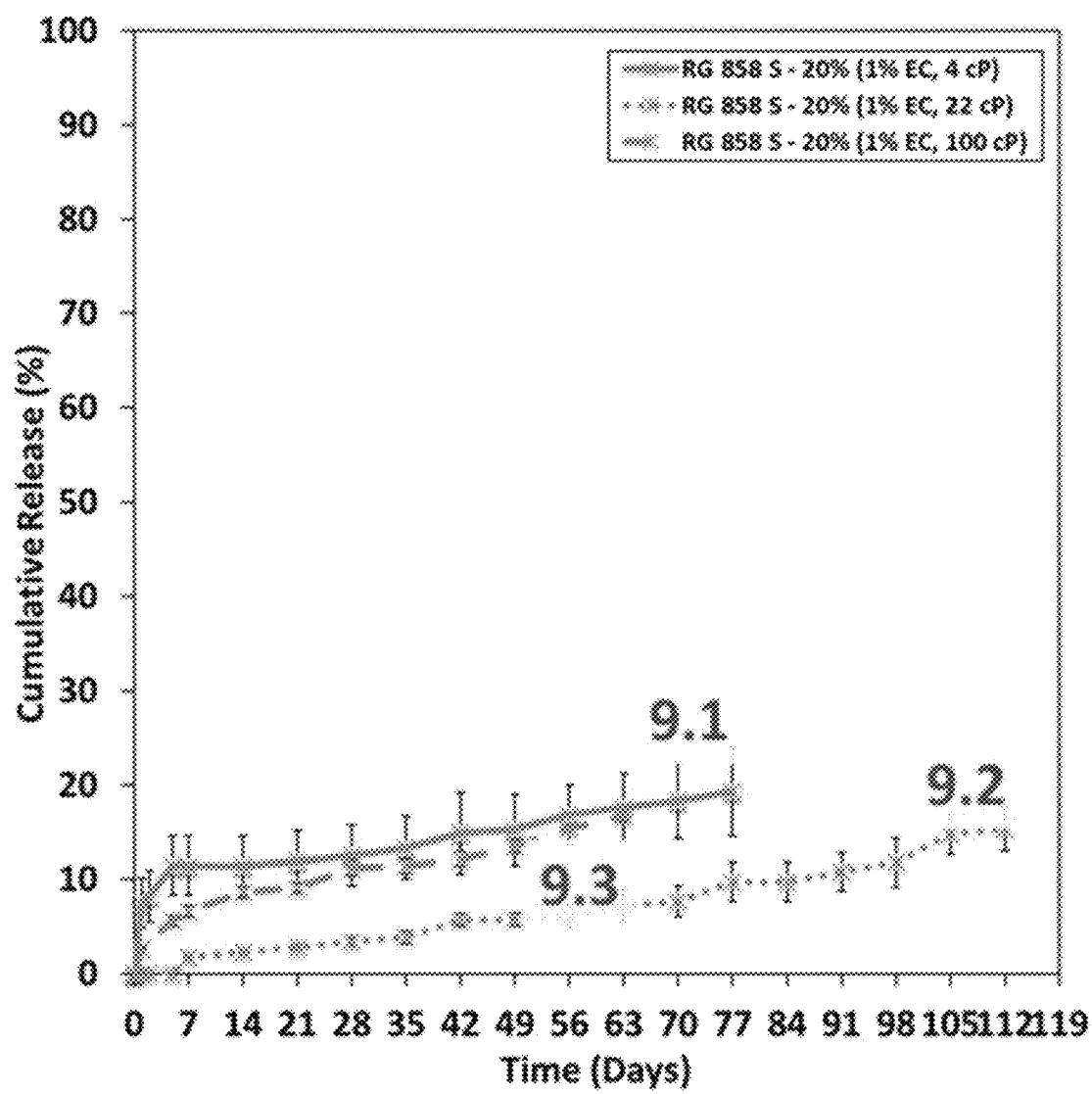
FIG. 9 shows a plot of the cumulative release of the active ingredient from microspheres prepared in Example 9.

The data represented in FIG. 9 demonstrates that the viscosity of ethyl cellulose affects release rate of Drug C (FIG. 9).

Example 10

Monodisperse microspheres were fabricated as described in Example 1, only using P-LL-G 82:18, Drug C, and varying viscosities of ethyl cellulose (Samples 10.1-10.3).

TABLE 10

| | Sample ID | | |
|---|---|---|---|
| | 10.1 | 10.2 | 10.3 |
| Polymer Type | P-LL-G | P-LL-G | P-LL-G |
| Co-Block Ratios (%-%) | 82-18 | 82-18 | 82-18 |
| Polymer Inherent Viscosity (dL/g) | 2.15 | 2.15 | 2.15 |
| Absolute Polymer Content (% w/w) | 81.30 | 81.18 | 80.30 |
| Relative Polymer Content in Matrix (%) | 98.75 | 98.75 | 98.75 |
| EC Kinematic Viscosity (cP) | 4 | 22 | 100 |
| EC Inherent Viscosity (dL/g) | 0.41 | 0.75 | 1.05 |
| Absolute EC Content (% w/w) | 1.02 | 1.02 | 1.01 |
| Relative EC Content in Matrix (% w/w) | 1.25 | 1.25 | 1.25 |
| EC Viscosity Fraction (%) | 0.24 | 0.44 | 0.61 |
| Drug | C | C | C |
| Absolute Drug Content (% w/w) | 17.68 | 17.80 | 18.69 |

Figure 10:
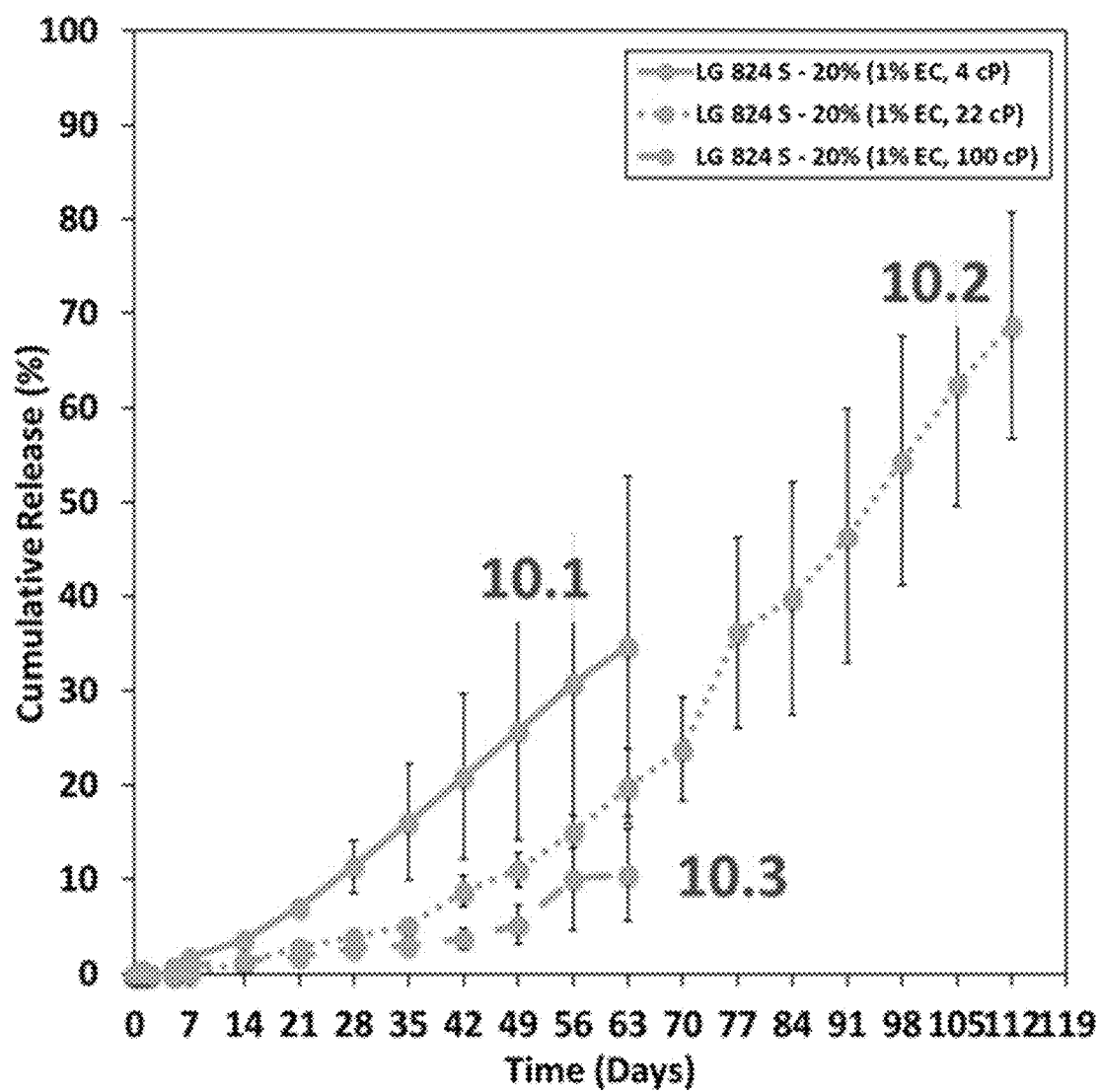
FIG. 10 shows a plot of the cumulative release of the active ingredient from microspheres prepared in Example 10.

The data represented in FIG. 10 demonstrate that the viscosity of ethyl cellulose affects release rate of Drug C.

Example 11

Monodisperse microspheres were fabricated as described in Example 1, only using poly(L-lactide-co-D,L-lactide) 70:30, Drug C, and varying viscosities of ethyl cellulose (Samples 11.1-11.3).

TABLE 11

| | Sample ID | | |
|---|---|---|---|
| | 11.1 | 11.2 | 11.3 |
| Polymer Type | P-LL-DLL | P-LL-DLL | P-LL-DLL |
| Co-Block Ratios (%-%) | 70-30 | 70-30 | 70-30 |
| Polymer Inherent Viscosity (dL/g) | 2.40 | 2.40 | 2.40 |
| Absolute Polymer Content (% w/w) | 80.25 | 82.54 | 79.46 |
| Relative Polymer Content in Matrix (%) | 98.75 | 98.75 | 98.75 |
| EC Kinematic Viscosity (cP) | 4 | 22 | 100 |
| EC Inherent Viscosity (dL/g) | 0.41 | 0.75 | 1.05 |
| Absolute EC Content (% w/w) | 1.01 | 1.04 | 1.00 |
| Relative EC Content in Matrix (% w/w) | 1.25 | 1.25 | 1.25 |
| EC Viscosity Fraction (%) | 0.21 | 0.39 | 0.55 |
| Drug | C | C | C |
| Absolute Drug Content (% w/w) | 18.74 | 16.42 | 19.54 |

Figure 11:
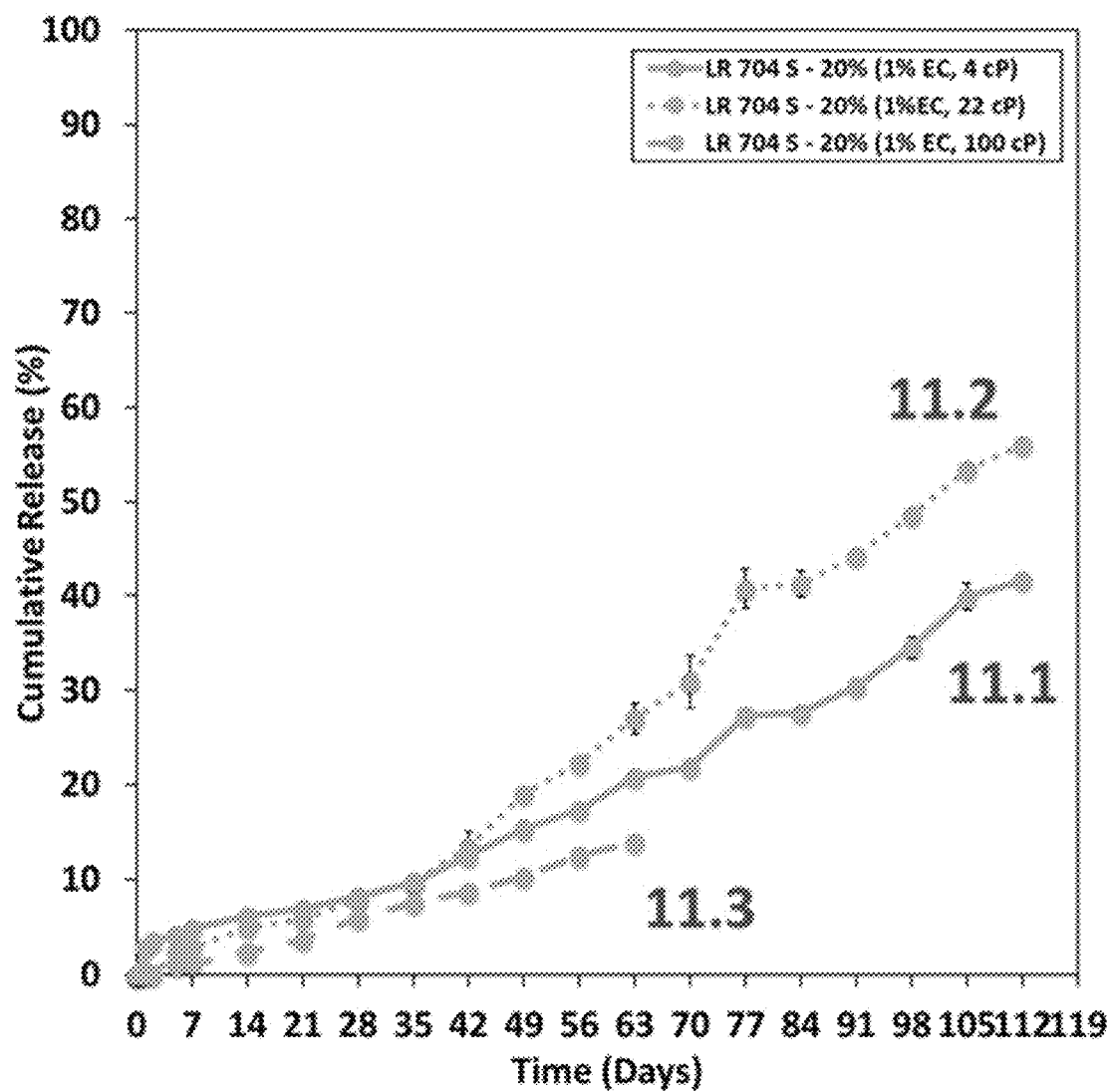
FIG. 11 shows a plot of the cumulative release of the active ingredient from microspheres prepared in Example 11.

The data represented in FIG. 11 demonstrates that the viscosity of ethyl cellulose affects release rate of Drug C.

The results of Examples 6 to 11 show that the release rate of the drug is influenced by the viscosity grade of the ethyl cellulose and the viscosity fraction that it contributes to the polymer matrix. Generally, the higher the viscosity fraction of EC in the matrix, the slower the release rate. Release rate is also affected by the percentage of drug contained in the formulation, with higher drug content providing faster release rates. As noted above, the glycolide content of the polymer may also impact the influence of the cellulose-derived material (CDM) on release rate. Other factors that may influence the release rates include viscosity matching between the polymer and the CDM, and the physical properties (i.e. water solubility) of the drug itself. Thus, it may be possible to prepare formulations with an appropriate polymer, cellulose material, and drug loading to provide a desired release profile for a given drug.

Example 12

Monodisperse microspheres were fabricated as described in Example 1, only using varying viscosities of P-DLL-G 85:15, P-DLL 100:0, combinations of P-DLL-G and P-DLL, Drug C, and one viscosity of ethyl cellulose (Samples 12.1-12.5).

TABLE 12

| | Sample ID | | | | |
|---|---|---|---|---|---|
| | 12.1 | 12.2 | 12.3 | 12.4 | 12.5 |
| Polymer Type | P-DLL-G | P-DLL-G | P-DLL-G | P-DLL | 10% P-DLL/ 90% P-DLL-G |
| Co-Block Ratios (%-%) | 85-15 | 85-15 | 85-15 | 100-0 | 100-0/85:15 |
| Polymer Inherent Viscosity (dL/g) | 0.70 | 0.70 | 1.50 | 1.50 | 1.50 |
| Absolute Polymer Content (% w/w) | 91.75 | 82.36 | 79.89 | 80.39 | 80.78 |
| Relative Polymer Content in Matrix (%) | 98.75 | 98.75 | 98.75 | 98.75 | 98.75 |
| EC Kinematic Viscosity (cP) | 22 | 22 | 22 | 22 | 22 |
| EC Inherent Viscosity (dL/g) | 0.75 | 0.75 | 0.75 | 0.75 | 0.75 |
| Absolute EC Content (% w/w) | 1.15 | 1.04 | 1.01 | 1.01 | 1.02 |

TABLE 12-continued

|  | Sample ID | | | | |
| --- | --- | --- | --- | --- | --- |
|  | 12.1 | 12.2 | 12.3 | 12.4 | 12.5 |
| Relative EC Content in Matrix (% w/w) | 1.25 | 1.25 | 1.25 | 1.25 | 1.25 |
| EC Viscosity Fraction (%) | 1.33 | 1.33 | 0.63 | 0.63 | 0.63 |
| Drug | C | C | C | C | C |
| Absolute Drug Content (% w/w) | 7.10 | 16.60 | 19.10 | 18.60 | 18.20 |

Figure 12A:
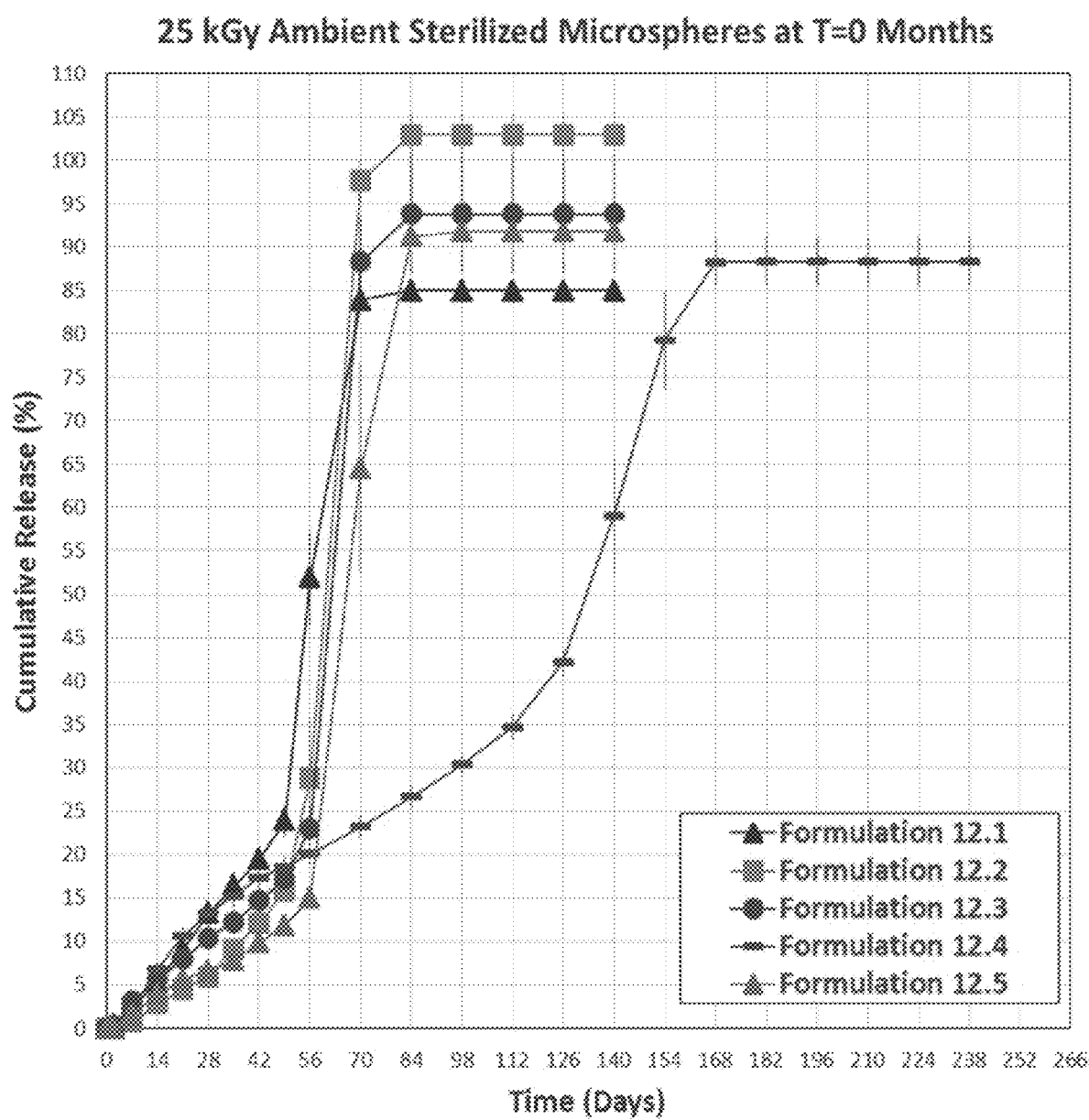
FIGS. 12A to 12C show plots of the cumulative release of the active ingredient from microspheres prepared in Example 12 and stored at elevated temperatures.
Figure 12B:
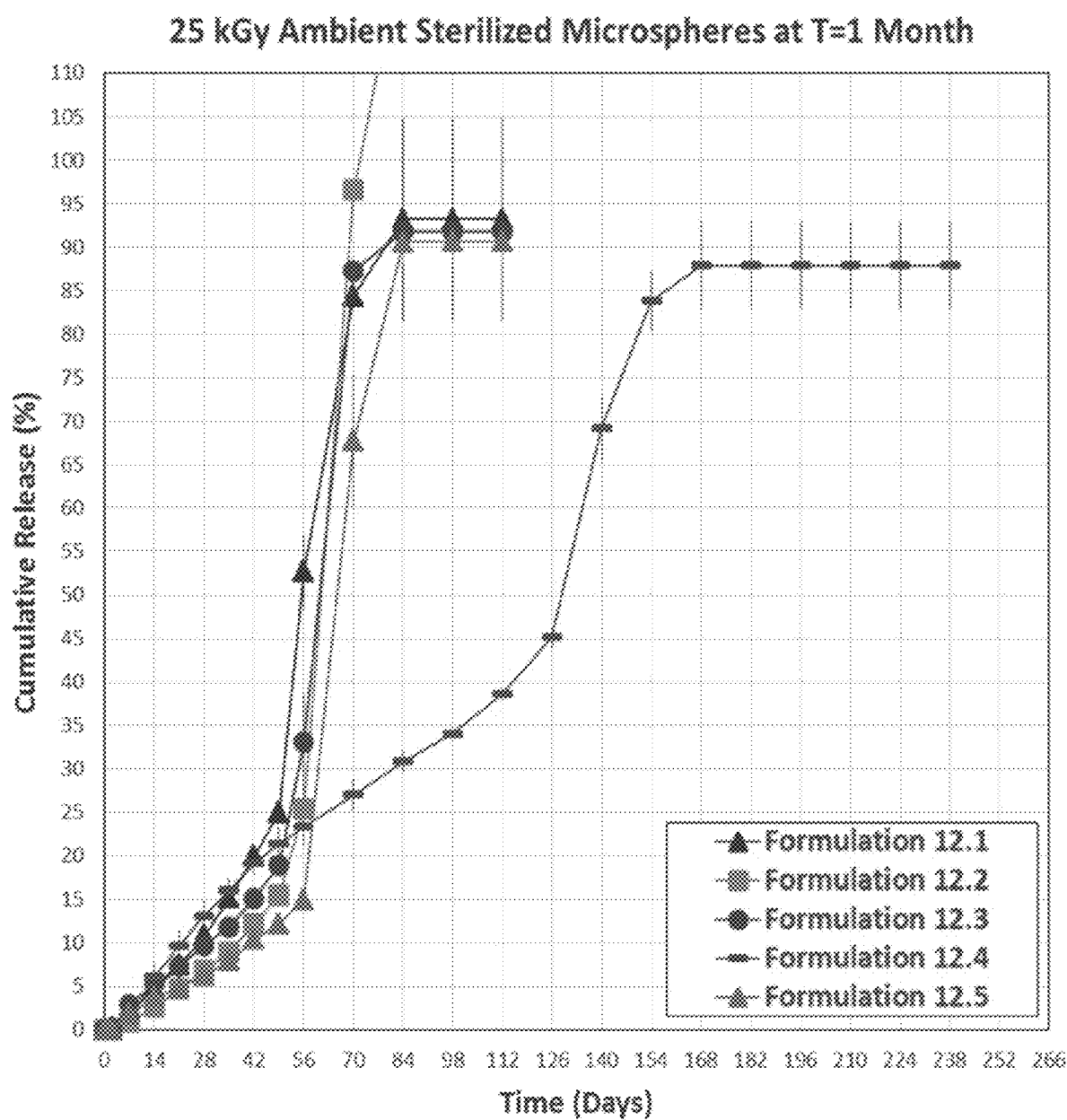
Figure 12C:
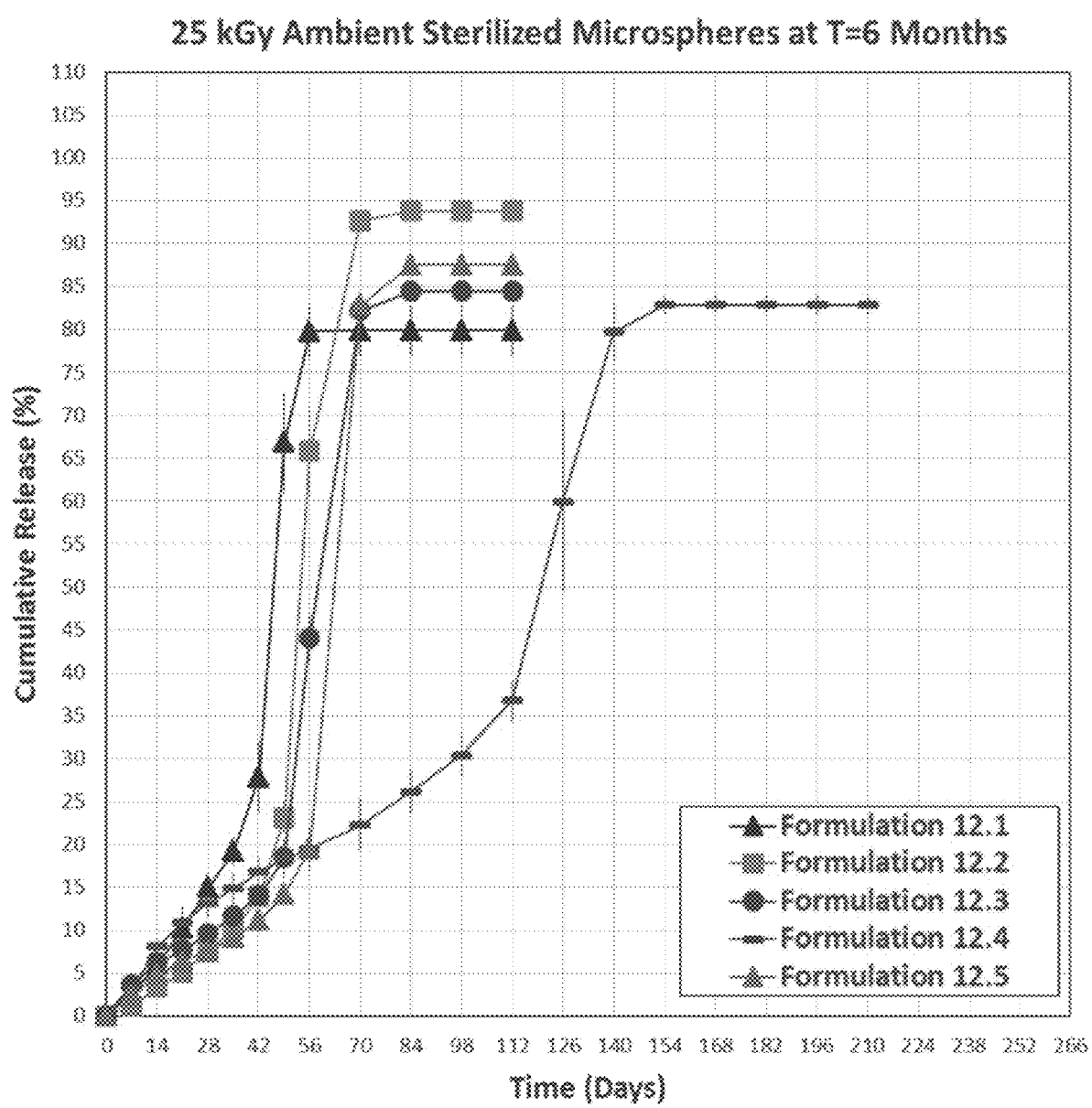

The data represented in FIGS. 12A to 12C demonstrate that inclusion of ethyl cellulose improves microsphere dissolution reproducibility after stability testing at 40° C. and 75% RH in sealed glass vials for 0, 1 month and 6 months, where no drug burst is present in any formulation. Formulations 12.1, 12.2 and 12.3 each exhibited release profiles showing relatively steady release rates up to around 40 to 55 days, followed by much faster release rates until the cumulative release plateaued at around 70 days. Without being bound by theory, the faster release rate may be due to disruption of the physical integrity of the microspheres caused by hydrolytic degradation of the polymer and/or mechanical erosion of the microspheres. Formulation 12.4, comprising a PLA rather than a PLGA as the major polymer had a similar, albeit slower release profile, with the breakpoint between the slower and faster release rates at about 110 days and the maximum release at about 155 days. Formulation 12.5, comprising a small amount of PLA mixed with PLGA, showed a release rate profile that is slightly extended compared to the samples without PLA. As in the previous examples, the release profile is also influenced by drug loading, having higher cumulative release with higher loading (compare 12.2 to 12.1).

Recommended storage conditions for PLA and PLGA-based formulations call for storage at −20° C. Surprisingly, each of the formulations tested show generally similar release profiles despite differing lengths of storage time at elevated temperatures, demonstrating good formulation stability even with extended storage at 40° C.

Example 13

Monodisperse microspheres were fabricated as described in Example 1, only using P-DLL-G 50:50, and Drug D with and without ethyl cellulose (Samples 13.1-13.2).

TABLE 13

|  | Sample ID | |
| --- | --- | --- |
|  | 13.1 | 13.2 |
| Polymer Type | P-DLL-G | P-DLL-G |
| Co-Block Ratios (%-%) | 50-50 | 50-50 |
| Polymer Inherent Viscosity (dL/g) | 0.38 | 0.38 |
| Absolute Polymer Content (% w/w) | 88.00 | 87.41 |
| Relative Polymer Content in Matrix (%) | 100.00 | 98.75 |
| EC Kinematic Viscosity (cP) | — | 22 |
| EC Inherent Viscosity (dL/g) | — | 0.75 |
| Absolute EC Content (% w/w) | — | 1.09 |
| Relative EC Content in Matrix (% w/w) | — | 1.25 |
| EC Viscosity Fraction (%) | — | 2.43 |
| Drug | D | D |
| Absolute Drug Content (% w/w) | 12.00 | 11.50 |

Figure 13:
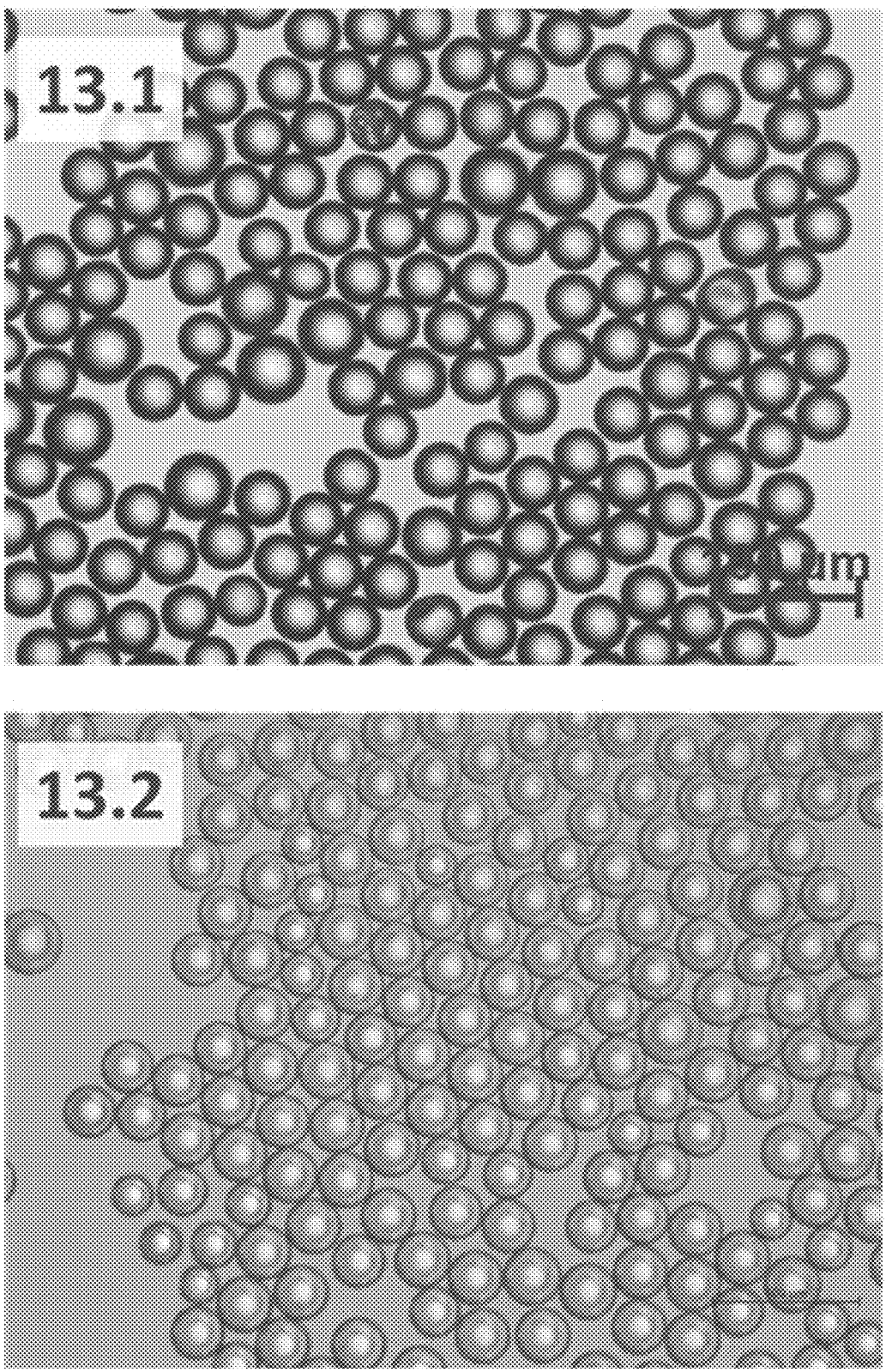
FIG. 13 shows photomicrographs of microspheres prepared in Example 13.

The data represented in FIG. 13 demonstrates that inclusion of ethyl cellulose improves microsphere size distribution of a very water soluble peptide.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Features of the disclosed embodiments may be combined, rearranged, omitted, etc., within the scope of the invention to produce additional embodiments. Furthermore, certain features may sometimes be used to advantage without a corresponding use of other features. Furthermore, no limitations are intended to the details of construction or design herein shown, other than as described in the claims below. It is therefore evident that the particular illustrative embodiments disclosed above may be altered or modified and all such variations are considered within the scope and spirit of this invention.

What is claimed is:

1. A composition for parenteral administration comprising:
    a plurality of microspheres,
    wherein each microsphere comprises a polymer matrix and an active therapeutic agent,
    wherein the polymer matrix comprises a homogenous mixture of a biodegradable polymer and a cellulose-derived material selected from the group consisting of cellulose ethers and cellulose esters,
    wherein the biodegradable polymer has a molecular weight of greater than 10,000 Daltons,
    wherein the percentage of active therapeutic agent is from about 10% to about 40% w/w of each microsphere,
    wherein the biodegradable polymer comprises a polyester polymer comprising a co-block polymer selected from the group consisting of poly(D,L-lactide-co-glycolide) and poly(L-lactide-co-glycolide),
    wherein the percentage of biodegradable polymer is from about 50% to about 95% w/w of each microsphere,
    wherein the cellulose-derived material comprises ethyl cellulose,
    wherein the percentage of cellulose-derived material is from about 0.5% to about 6% w/w of each microsphere, and
    wherein the cellulose-derived material (CDM) comprises a viscosity fraction of about 0.1% to about 5%.

2. The composition of claim 1, wherein the biodegradable polymer is selected from the group consisting of a bulk-eroding polymer, a surface-eroding polymer, and a polyanhydride polymer.

3. The composition of claim 1, wherein the co-block polymer is poly(D,L-lactide-co-glycolide) and wherein the percentage of lactide is from about 50% to about 80% w/w of the co-block polymer and wherein the percentage of glycolide is from about 20% to about 50% w/w of the co-block polymer.

4. The composition of claim 1, wherein the co-block polymer is poly(L-lactide-co-glycolide) and wherein the percentage of lactide is from about 50% to about 80% w/w of the co-block polymer and wherein the percentage of glycolide is from about 20% to about 50% w/w of the co-block polymer.

5. The composition of claim 1, wherein the cellulose-derived material further comprises one or more of carboxymethyl cellulose, hydroxypropylmethyl cellulose, and sodium carboxymethyl cellulose.

6. The composition of claim 1, wherein the active therapeutic agent is selected from the group consisting of an integrase inhibitor, an antiparasitic, a steroid hormone, and a somatostatin analogue.

7. The composition of claim 1, wherein the active therapeutic agent is an organic compound having a molecular weight of less than 1000 daltons.

8. The composition of claim 1, further comprising a pharmaceutically acceptable carrier, excipient or diluent.

9. The composition of claim 1, wherein the composition comprises at least one member selected from the group consisting of an aqueous solution and a buffer solution.

10. The composition of claim 9, further comprising a pharmaceutical surfactant.

11. The composition of claim 9, further comprising a cryoprotectant.

12. A method for treating a subject having a disease or condition indicating a need for treatment comprising parenteral administration, the method comprising administering a composition of claim 1 to the subject parenterally.

13. The composition of claim 1, wherein at least 90% of the plurality of microspheres have a particle diameter from about 40 µm to about 70 µm.

14. The composition of claim 1, wherein at least 90% of the plurality of microspheres have a particle diameter from about 50 µm to about 60 µm.

15. The composition of claim 1, wherein at least 50% of the active therapeutic agent is released from the microspheres over a period of at least 50 days.

16. The composition of claim 1, wherein the active therapeutic agent is released from the microspheres over a period of from 100 to about 120 days.

* * * * *